(12) United States Patent
Konduri et al.

(10) Patent No.: US 12,251,469 B2
(45) Date of Patent: Mar. 18, 2025

(54) STERICALLY STABILIZED CARRIER COMPOSITIONS FOR TREATING A MAMMAL

(71) Applicant: VGSK Technologies, Inc., Madison, WI (US)

(72) Inventors: Kameswari S. Konduri, Madison, WI (US); Nejat Duzgunes, Mill Valley, CA (US); Jogi Pattisapu, Orlando, FL (US); Ram Pattisapu, Silverthorne, CO (US)

(73) Assignee: VGSK Technologies, Inc., Madison, WI (US)

( * ) Notice: Subject to any disclaimer, the term of this patent is extended or adjusted under 35 U.S.C. 154(b) by 0 days.

(21) Appl. No.: 18/403,360

(22) Filed: Jan. 3, 2024

(65) Prior Publication Data
US 2024/0180835 A1   Jun. 6, 2024

Related U.S. Application Data

(63) Continuation of application No. 17/571,049, filed on Jan. 7, 2022, now abandoned, which is a continuation of application No. 15/759,651, filed as application No. PCT/US2016/051759 on Sep. 14, 2016, now abandoned.

(60) Provisional application No. 62/218,558, filed on Sep. 14, 2015.

(51) Int. Cl.
| | |
|---|---|
| *A61K 9/127* | (2006.01) |
| *A61K 9/1271* | (2025.01) |
| *A61K 31/573* | (2006.01) |
| *A61K 31/58* | (2006.01) |
| *A61K 45/06* | (2006.01) |
| *A61K 47/34* | (2017.01) |
| *A61P 29/00* | (2006.01) |
| *A61P 31/06* | (2006.01) |
| *A61P 37/08* | (2006.01) |

(52) U.S. Cl.
CPC ............ *A61K 9/1271* (2013.01); *A61K 9/127* (2013.01); *A61K 31/573* (2013.01); *A61K 31/58* (2013.01); *A61K 45/06* (2013.01); *A61K 47/34* (2013.01); *A61P 29/00* (2018.01); *A61P 31/06* (2018.01); *A61P 37/08* (2018.01)

(58) Field of Classification Search
CPC ........ A61K 45/06; A61K 47/34; A61K 9/127; A61K 9/1271; A61P 29/00; A61P 31/06; A61P 37/08
See application file for complete search history.

(56) References Cited

U.S. PATENT DOCUMENTS

| | | |
|---|---|---|
| 5,013,556 A | 5/1991 | Woodle et al. |
| 5,356,633 A | 10/1994 | Woodle et al. |
| 5,824,761 A | 10/1998 | Bujanowski et al. |
| 5,891,468 A | 4/1999 | Martin et al. |
| 5,958,378 A | 9/1999 | Waldrep et al. |
| 5,965,434 A | 10/1999 | Wolff et al. |
| 6,197,333 B1 | 3/2001 | Onyuksel et al. |
| 6,203,822 B1 | 3/2001 | Schlesinger et al. |
| 6,461,591 B1 | 10/2002 | Keller et al. |
| 6,562,371 B1 | 5/2003 | Kawahara et al. |
| 6,566,324 B2 | 5/2003 | Nadel et al. |
| 6,660,525 B2 | 12/2003 | Martin et al. |
| 6,824,761 B1 | 11/2004 | Hills et al. |
| 8,062,662 B2 | 11/2011 | Lasic et al. |
| 8,846,079 B1 | 9/2014 | Konduri et al. |
| 11,324,698 B2 | 5/2022 | Konduri et al. |
| 2002/0009488 A1 | 1/2002 | Francis et al. |
| 2002/0106330 A1 | 8/2002 | Waldrep et al. |
| 2002/0110587 A1 | 8/2002 | Rodrigueza et al. |
| 2002/0131995 A1 | 9/2002 | Szoka, Jr. |
| 2002/0156062 A1 | 10/2002 | Boch et al. |
| 2003/0147945 A1 | 8/2003 | Tardi et al. |
| 2004/0037875 A1 | 2/2004 | Metselaar et al. |
| 2004/0076691 A1 | 4/2004 | Haines et al. |
| 2004/0097471 A1 | 5/2004 | Maring et al. |
| 2004/0110695 A1 | 6/2004 | Dobbie |
| 2005/0202078 A1 | 9/2005 | Schiffelers et al. |
| 2006/0115523 A1 | 6/2006 | Konduri et al. |
| 2006/0251711 A1 | 11/2006 | Konduri et al. |
| 2011/0244029 A1 | 10/2011 | Barenholz et al. |
| 2015/0071988 A1 | 3/2015 | Konduri et al. |
| 2016/0228573 A1 | 8/2016 | Niyikiza et al. |
| 2018/0169263 A1 | 6/2018 | Hanes et al. |
| 2019/0046444 A1 | 2/2019 | Konduri et al. |
| 2020/0352859 A1 | 11/2020 | Konduri et al. |

(Continued)

FOREIGN PATENT DOCUMENTS

| | | |
|---|---|---|
| EP | 2638896 A1 | 9/2013 |
| WO | WO-03040308 A2 | 5/2003 |

(Continued)

OTHER PUBLICATIONS

Ajay Kumar Thakur et al.: Patented therapeutic drug delivery strategies for targeting pulmonary diseases, Expert Opinion on Therapeutic Patents, 2020, 1744-7674.
Barnes et al.: Inflammatory mechanisms in patients with chronic obstructive pulmonary disease. J Allergy Clin Immunol. 138:16-27 (2016).
Beigel et al.: Remdesivir for the Treatment of Covid-19—Final Report. N Engl J Med. 383(19):1-14 (2020).
European Search Report dated May 28, 2019 for EP Application No. 16847243.9.
Gangadharam et al.: Therapy of *Mycobacterium avium* Complex Infections in Beige Mice With Streptomycin Encapsulated in Sterically Stabilized Liposomes. Antimicrobial Agents and Chemotherapy 39(3):725-730 (1995).
Health Desk: Is there a cure for COVID-19? What is the cure? (2021).

(Continued)

*Primary Examiner* — Kara R. McMillian
(74) *Attorney, Agent, or Firm* — WILSON SONSINI GOODRICH & ROSATI

(57) ABSTRACT

Disclosed herein are pharmaceutical compositions and methods for oral or sublingual administration comprising sterically stabilized liposome carriers which release in different pHs in a subject. Compositions and methods for treatment of allergies, eosinophilic esophagitis, inflammation, tuberculosis and other diseases are also described.

20 Claims, 14 Drawing Sheets

(56) References Cited

U.S. PATENT DOCUMENTS

| | | | |
|---|---|---|---|
| 2022/0331249 | A1 | 10/2022 | Konduri et al. |
| 2023/0029342 | A1 | 1/2023 | Konduri et al. |
| 2023/0270756 | A1 | 8/2023 | Kameswari et al. |

FOREIGN PATENT DOCUMENTS

| | | |
|---|---|---|
| WO | WO-03046145 A2 | 6/2003 |
| WO | WO-03105765 A2 | 12/2003 |
| WO | WO-2010045479 A1 | 4/2010 |
| WO | WO-2013066179 A1 | 5/2013 |
| WO | WO-2017048860 A1 | 3/2017 |

OTHER PUBLICATIONS

Hong MS, et al, pH-sensitive, serum-stable and long-circulating liposomes as a new drug delivery system, J Pharm Pharmacol. Jan. 2002;54(1):51-8. doi: 10.1211/0022357021771913. PMID: 11829129.

Immordino, Maria Laura et al. Stealth liposomes: review of the basic science, rationale, and clinical applications, existing and potential. International journal of nanomedicine vol. 1,3 (2006): 297-315.

International Search Report for Application No. PCT/US2016/051759 dated Nov. 30, 2016.

Kanae Ichikawa et al.: Suppression of immune response by antigen-modified liposomes encapsulating model agents: A novel strategy from the treatment of allergy, Journal of Controlled Release, vol. 167, p. 284-289, 2013.

Konduri, et al. Budesonide Delivered in Sterically Stabilized Liposomes Decreases Airway Hyperresponsiveness to Methacholine. Presented at the Annual AAAAI Meeting, Denver, CO., Mar. 2003. 19 pages.

Konduri, et al. Efficacy of Liposomal Budesonide in Experimental Asthma abstract presented at the Annual AAAAI meeting, New Orleans, LA, 2001. Published in Journal of Allergy Clinical Immunology, vol. 111, No. 2, 2003. 7 pages.

Konduri et al.: Efficacy of Liposome Encapsulated Budesonide in Experimental Asthma. Abstract 1029. Journal of Allergy Clinical Immunology 107(2): S315 (2001).

Konduri et al.: Prolung™—budesonide Inhibits SARS-CoV-2 Replication and Reduces Lung Inflammation. Archives of Pharmacology Therapeutics. 3(2):52-65 (2021).

Kulig W. et al.: How well does cholesteryl hemisuccinate mimic cholesterol in saturated phospholipid bilayers? J Mol Model. Feb. 2014;20(2):2121.

Mahase et al.: Covid-19: Budesonide shortens recovery time in patients not admitted to hospital, study finds. BMJ. 373:n957; http://dx.doi.org/10.1136/bmj.n57 (2021).

Milne et al.: Inhaled corticosteroids downregulate SARS-CoV-2-related gene expression in COPD: results from a RCT. medRxiv. 58(1):2100130 (2020).

M.M. Gaspar et al.: Rifabutin encapsulated in liposomes exhibits increased therapeutic activity in a model of disseminated tuberculosis, International Journal of Antimicrobial Agents, vol. 31, p. 37-45, 2008.

Monali, Manohar, Potential of Anti-Ige in Food Allergy Therapy, Current Treatment Options i Allergy, vol. 1, No. 2, Mar. 2014, pp. 145-156.

Noel K.Childers et al.: Adjuvant Activity of Monophosphoryl Lipid A for Nasal and Oral Immunization with Soluble or Liposome-Associated Antigen, Infection and Immunity, Oct. 2000, vol. 68, No. 10, p. 5509-5516, 0019-9567/00304.00+0.

Núria Almiñana et al.: Biodistribution Study of Doxorubicin Encapsulated in Liposomes: Influence of Peptide Coating and Lipid Composition, Preparative Biochemistry and Biotechnology, vol. 34, No. 1, p. 77-96, 2004.

PCT/US2022/027838 International Preliminary Report on Patentability dated Nov. 16, 2023.

PCT/US2022/027838 International Search Report and Written Opinion dated Jul. 11, 2022.

Ramakrishnan et al.: Inhaled budesonide in the treatment of early COVID-19 (STOIC): a phase 2, open-label, randomized controlled trial. The Lancet Respiratory Medicine. 9(7):763-772 (2021).

Schreier. Chapter 6.3: Pulmonary applications of liposomes. Medical Applications of Liposomes. D.D. Lasic and D. Papahadjopoulos. (pp. 474-475) (1998).

Upendra Bulbake et al.: Liposomal Formulations in Clinical Use: An updated Review, Pharmaceutics, 2017, 9, 12, pp. 1-33.

U.S. Appl. No. 12/218,777 Notice of Allowance dated May 16, 2014.

U.S. Appl. No. 12/218,777 Office Action dated Apr. 18, 2011.

U.S. Appl. No. 12/218,777 Office Action dated Aug. 23, 2011.

U.S. Appl. No. 12/218,777 Office Action dated Sep. 11, 2013.

U.S. Appl. No. 14/453,125 Office Action dated Feb. 8, 2017.

U.S. Appl. No. 14/453,125 Office Action dated Aug. 22, 2017.

U.S. Appl. No. 14/453,125 Office Action dated Apr. 5, 2018.

U.S. Appl. No. 15/759,651 Final Office Action dated Jun. 11, 2020.

U.S. Appl. No. 15/759,651 Non-Final Office Action dated Aug. 5, 2021.

U.S. Appl. No. 15/759,651 Non-Final Office Action dated Sep. 13, 2019.

U.S. Appl. No. 18/120,770 Office Action dated Jan. 4, 2024.

Xue-Qing Wang and Qiang Zhang, pH-sensitive polymeric nanoparticles to improve oral bioavailability of peptide/protein drugs and poorly water-soluble drugs, European Journal of Pharmaceutics and Biopharmaceutics, vol. 82, Issue 2, Oct. 2012, pp. 219-229.

Zhu, Guodong et al. Secretory phospholipase $A_2$ responsive liposomes. Journal of pharmaceutical sciences vol. 100,8 (2011): 3146-3159. doi:10.1002/jps.22530.

STERICALLY STABILIZED CARRIER COMPOSITIONS FOR TREATING A MAMMAL

CROSS-REFERENCE

This application is a continuation of U.S. patent application Ser. No. 17/571,049, filed Jan. 7, 2022, which is a continuation of Ser. No. 15/759,651, filed Mar. 13, 2018, which claims the benefit to PCT International Patent Application PCT/US2016/051759, filed Sep. 14, 2016, which claims the benefit of U.S. Provisional Application No. 62/218,558, filed Sep. 14, 2015, which application is incorporated herein by reference in its entirety.

STATEMENT AS TO FEDERALLY SPONSORED RESEARCH

This invention was made with government support under Grant no. 1R41HL73668-1A1 awarded by National Heart, Lung and Blood Institute. The government has certain rights in the invention.

BACKGROUND OF THE INVENTION

Many existing methods and compositions for delivering therapeutics and treating disease states are not entirely satisfactory. For example, a major draw back of using conventional liposomes in treating disease states is that they have a relatively short life in a mammal body. Accordingly, there is a need for new and improved methods and compositions. Compositions, methods, and kits of using a sterically stabilized liposome carrier can be used to extend the life of liposomes in a mammal body. Also, most applications of conventional liposomes are in the bloodstream. Also disclosed herein are methods of subcutaneously, sublingually, or orally administering a pharmaceutical composition, which comprises a sterically stabilized liposome carrier.

Food allergies and more specifically IgE mediated food allergies represent a growing concern among industrialized countries, and it is estimated that these allergies currently affect up to 4% of the population of westernized countries and 6-8% of young children. In contrast to the increasing number of treatments for airway allergies, the therapeutic approach for food allergy remains very limited.

SUMMARY OF THE INVENTION

Disclosed herein are compositions, kits, and methods of using a sterically stabilized liposome carrier for treating a condition or disorder. In one aspect, disclosed herein is a method for treating inflammation associated with an allergy or a disease in a subject in need thereof, the method comprising administering, orally or sublingually, (1) a first active agent encapsulated in a first liposome carrier that comprises: i) poly (ethylene glycol) distearoylphosphatidylethanolamine (PEG-DSPE), ii) phosphatidylglycerol, phosphatidylcholine, or a combination thereof, and a pH sensitive component which causes the liposome to release the first active agent in a pH range of about pH 1 to about pH 5; and (2) a second active agent encapsulated in a second liposome carrier that comprises: i) poly (ethylene glycol) distearoylphosphatidylethanolamine (PEG-DSPE), ii) phosphatidylglycerol, phosphatidylcholine, or a combination thereof, wherein the second liposome carrier releases the second active agent in a pH range of about pH 6 to about pH 8. In some embodiments, the pH sensitive component comprises an acylated amino acid, a phospholipid, a fatty acid, a double chain amphiphile, cholesteryl hemisuccinate, or any combination thereof. In some embodiments, the pH sensitive component comprises N-palmitoyl homocysteine (PHC).

In some embodiments, the first active agent, the second active agent, or both the first active agent and the second active agent comprise a proton pump inhibitor, a corticosteroid, an antihistamine, a bronchodilator, a mast cell stabilizer, a leukotriene inhibitor, an allergen, an anti-inflammatory agent, or any combination thereof. In some embodiments, the anti-inflammatory agent comprises theophylline, budesonide, flunisolide, triamcinolone, beclomethasone, fluticasone, mometasone, dexamethasone, hydrocortisone, methylprednisolone, prednisone, cortisone, or betamethasone, or any combination thereof.

In some embodiments, the first active agent and the second active agent are the same. In some embodiments, the first active agent and the second active agent are different.

In some embodiments, the method or composition is used for treating inflammation associated with an allergy. In some embodiments, the allergy is a food allergy, and wherein the first active agent comprises peanut, tree nut, egg, shellfish, soy, milk, gluten, or any combination thereof.

In some embodiments of the methods and compositions described herein, the first active agent, the second active agent, or both the first active agent and the second active agent comprise an H1-antihistamine, H2-antihistamine, H3-antihistamine, H4-antihistamine, or any combination thereof. In some embodiments, the H1-antihistamine comprises acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine, pheniramine, phenyltoloxamine, promethazine, quetiapine, rupatadine, tripelennamine, triprolidine, or any combination thereof.

In some embodiments, the first liposome carrier comprises from about 60% to about 99% phosphatidylcholine, phosphatidylglycerol, or combination thereof. In some embodiments, the second liposome carrier comprises from about 60% to about 99% phosphatidylcholine, phosphatidylglycerol, or combination thereof.

In some embodiments, the first liposome carrier and the second liposome carrier comprise about 1% to about 5% PEG-DSPE. In some embodiments, the first liposome carrier and the second liposome carrier comprise about 1% to about 33% of the first active agent.

In some embodiments of the compositions and methods provided herein, the first active agent, the second active agent, or both the first active agent and the second active agent comprise an anti-tuberculosis agent. In some embodiments, the first active agent, the second active agent, or both the first active agent and the second active agent comprise an anti-IgE antibody or a fragment thereof.

In some embodiments, the first active agent, the second active agent, or both the first active agent and the second active agent is in a form of a lyophilized powder.

In some embodiments, methods and compositions described herein are used for treating inflammation associated with an allergy or a disease in a subject in need thereof. In some embodiments, the disease is a chronic immune system disease. In some embodiments, the disease is tuberculosis. In some embodiments, the disease is Eosinophilic esophagitis (EoE).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
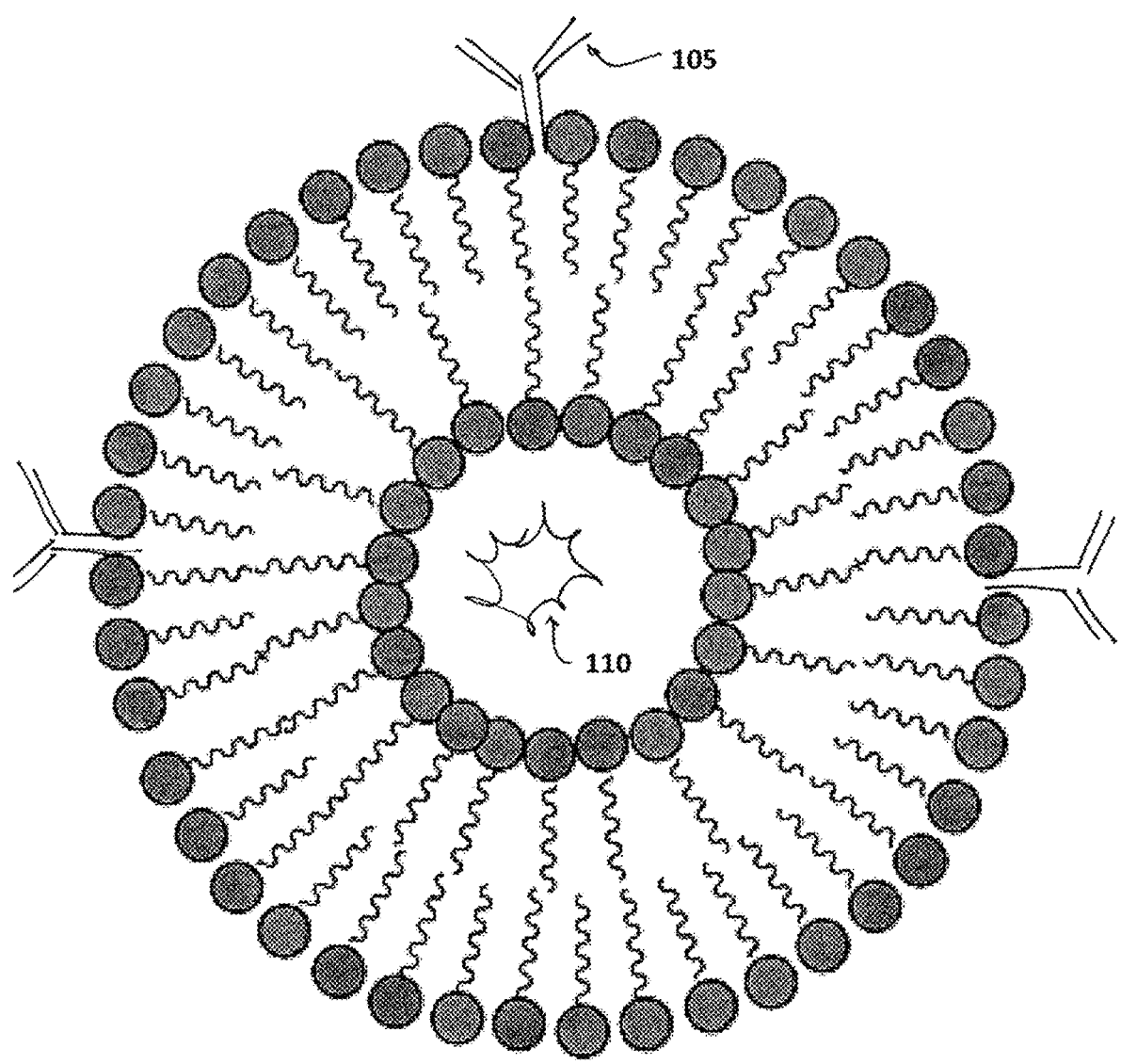
FIG. 1 depicts a structure of a sterically stabilized liposome carrier having at least a membrane portion and an interior portion.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some embodiments herein contemplate numerical ranges. When a numerical range is provided, unless otherwise indicated, the range includes the range endpoints. Unless otherwise indicated, numerical ranges include all values and subranges therein as if explicitly written out.

The term "about" and its grammatical equivalents in relation to a reference numerical value and its grammatical equivalents as used herein can include a range of values plus or minus 10% from that value. For example, the amount "about 10" includes amounts from 9 to 11. The term "about" in relation to a reference numerical value can also include a range of values plus or minus 10%, 9%, 8%, 7%, 6%, 5%, 4%, 3%, 2%, or 1% from that value.

Unless otherwise indicated, the ratios used herein are expressed as molar ratios. Unless otherwise indicated, the percentages used herein are expressed as molar percentages.

Overview

Disclosed herein are compositions, kits, and methods of using a sterically stabilized liposome carrier for treating a condition or disorder. In some cases, the condition is an allergy, for instance a food allergy. As such, in some embodiments are provided compositions and methods for the treatment of Immunoglobulin E (IgE)-mediated food allergy. In some embodiments, the food allergy is not characterized by airway inflammations.

In some cases, are provided compositions and methods for treating an inflammatory condition in a subject, wherein the inflammatory condition is not an airway inflammation. In some cases, the inflammatory condition is caused by eosinophilic esophagitis (EoE) or tuberculosis (TB). In some cases, the compositions, kits, and methods described herein can be used for treating more than one condition. The compositions, kits, and methods can be used to treat an inflammatory disorder and an allergy. The compositions, kits, and methods can be used to treat eosinophilic esophagitis and an allergy.

Subject

A "subject", as used herein, can be a mammal, preferably human. The subject can be diagnosed with a condition. In some cases, the condition is an allergy. In some cases, the condition is an inflammatory disorder. In some cases, the condition is eosinophilic esophagitis (EoE). In some cases, the condition is tuberculosis (TB). In some cases, the condition is not asthma. In some cases, the condition is not allergic asthma.

The subject can be a male or a female. The subject can be patients of any age. The subject can be an adult, child, or newborn. For example, the subject may be a patient of at least about 1, 5, 10, 20, 30, 40, 50, 60, 70, 80, 90, or 100 years old. For example, the subject can be a patient of less than about 10 years old. Often, the subject is a patient or other individual undergoing a treatment regimen, or being evaluated for a treatment regimen (e.g., allergen immunotherapy). However, in some instances, the subject is not undergoing a treatment regimen.

Compositions

Disclosed herein are pharmaceutical compositions particularly suitable for oral, subcutaneous, sublingual or buccal administration, comprising a sterically stabilized liposome carrier. Compositions described herein can provide sustained slow release of an agent formulated with a sterically stabilized liposome carrier described herein, and in certain embodiments can be administered orally, subcutaneously or sublingually about once a week. In some embodiments, the sterically stabilized liposome carrier can be spherical vesicles having at least one lipid bilayer. The sterically stabilized liposome carrier can comprise phospholipids and can encapsulate a variety of drugs, therapeutic agents and/or allergens in amounts specifically suited for oral, subcutaneous or sublingual delivery. In certain embodiments, the sterically stabilized liposome carrier can also be used to encapsulate allergens to treat allergy, for instance food allergy.

In certain embodiments, sterically stabilized liposome carriers described herein can have various interactions with cells upon administration to a subject. In some cases, the sterically stabilized liposome carrier can exchange materials, such as lipids, lipids and proteins with cell membranes. In some cases, the sterically stabilized liposome carrier can transfer encapsulated therapeutic agents to the cell. In some cases, the sterically stabilized liposome carrier can be absorbed to cells. In some cases, the sterically stabilized liposome carrier can bind to cells. In some cases, the sterically stabilized liposome carrier can be internalized by cells via endocytosis or phagocytosis once bound to the cells. In some cases, the sterically stabilized liposome carrier can fuse to cell membranes once bound.

The sterically stabilized liposome carrier described herein can be used to extend the life of conventional liposomes in a mammalian body. Conventional liposomes are composed of naturally-occurring phospholipids, such as phosphatidylglycerol and phosphatidylcholine. Conventional liposomes can be recognized in vivo by the cells of the reticuloendothelial system and can be cleared rapidly from the circulation. In addition, incorporation of certain therapeutic agents, such as triamcinolone (TRJ) or beclomethasone, into conventional liposomes can result in their rapid redistribution and leakage from liposomes into the medium. In contrast to conventional liposomes, the sterically stabilized liposomes described herein can exhibit increased stability in plasma and decreased uptake by the reticuloendothelial system.

In certain embodiments, sterically stabilized liposome carrier described herein can retain drugs, therapeutic agents or allergens for a predetermined period of time. In some cases the predetermined period of time is 1, 2, 3, 4, 5, 6, 7 or 8 days. In some cases, the composition of the sterically stabilized liposome carrier can facilitate the encapsulation of a drug, therapeutic agent or allergen within the bilayer or inside the carrier. In some cases, the presence of sufficient amounts of PEGylated (PEG refers to poly(ethylene glycol)) lipids in the sterically stabilized liposome carrier can stabilize and protect the liposome from disruption upon exposure to biological milieu. In some cases, the composition comprises an amount of PEGylated lipid in the sterically stabilized liposome carrier, wherein the amount is sufficient to enable the drug, allergen or therapeutic agent to remain liposome-associated for a desired period of time. In some embodiments, the desired period of time is up to about one week.

In certain embodiments, sterically stabilized liposome carriers described herein can comprise poly(ethylene glycol) (PEG), phosphatidylglycerol (PG), phosphatidylcholine (PC), phosphatidylethanolamine (PE), phosphatidylserine (PS), phosphatidylinositol (PI), or any combination thereof. In some cases, the sterically stabilized liposome carrier can comprise poly(ethylene glycol) and phosphatidylglycerol. In some cases, the sterically stabilized liposome carrier can comprise poly(ethylene glycol) and phosphatidylcholine. In some cases, the sterically stabilized liposome carrier can comprise poly(ethylene glycol), phosphatidylglycerol, and/or phosphatidylcholine. The PEG component of the sterically stabilized liposome carrier can be poly (ethylene glycol) distearoylphosphatidylethanolamine (PEG-DSPE), PEG-dipalmitoylphosphatidylethanolamine (DPPE), PEG-di-C:15 PE, PEG-soy PE, or PEG-egg PE. In certain embodiments, the pharmaceutical composition is suitable for subcutaneous, sublingual, or oral administration. In some cases, the pharmaceutical composition is comprised in a lyophilized powder. In some cases, the pharmaceutical composition is deposited on a filter paper. In some cases, the pharmaceutical composition (e.g., lyophilized powder deposited on a filter paper) is reconstituted with a solvent, e.g., water, saline (e.g., 5% saline), or glycerol.

Sterically Stabilized Liposome Carrier

The PEG (e.g., PEG-DSPE), PG, or PC component of the sterically stabilized liposome carrier can have a molecular weight ranges from about 300 to about 6000 Daltons. For example, the PEG (e.g., PEG-DSPE), PG, or PC component of the sterically stabilized liposome carrier can have a molecular weight ranges from about 300 to about 500 Daltons, from about 300 to about 1000 Daltons, from about 300 to about 1500 Daltons, from about 300 to about 2000 Daltons, from about 300 to about 2500 Daltons, from about 300 to about 3000 Daltons, from about 300 to about 3500 Daltons, from about 300 to about 4000 Daltons, from about 300 to about 4500 Daltons, from about 300 to about 5000 Daltons, from about 300 to about 5500 Daltons, from about 300 to about 6000 Daltons, from about 400 to about 500 Daltons, from about 400 to about 1000 Daltons, from about 400 to about 1500 Daltons, from about 400 to about 2000 Daltons, from about 400 to about 2500 Daltons, from about 400 to about 3000 Daltons, from about 400 to about 3500 Daltons, from about 400 to about 4000 Daltons, from about 400 to about 4500 Daltons, from about 400 to about 5000 Daltons, from about 400 to about 5500 Daltons, from about 400 to about 6000 Daltons, from about 500 to about 1000 Daltons, from about 500 to about 1500 Daltons, from about 500 to about 2000 Daltons, from about 500 to about 2500 Daltons, from about 500 to about 3000 Daltons, from about 500 to about 3500 Daltons, from about 500 to about 4000 Daltons, from about 500 to about 4500 Daltons, from about 500 to about 5000 Daltons, from about 500 to about 5500 Daltons, from about 500 to about 6000 Daltons, from about 1000 to about 1500 Daltons, from about 1000 to about 2000 Daltons, from about 1000 to about 2500 Daltons, from about 1000 to about 3000 Daltons, from about 1000 to about 3500 Daltons, from about 1000 to about 4000 Daltons, from about 1000 to about 4500 Daltons, from about 1000 to about 5000 Daltons, from about 1000 to about 5500 Daltons, from about 1000 to about 6000 Daltons, from about 1500 to about 2000 Daltons, from about 1500 to about 2500 Daltons, from about 1500 to about 3000 Daltons, from about 1500 to about 3500 Daltons, from about 1500 to about 4000 Daltons, from about 1500 to about 4500 Daltons, from about 1500 to about 5000 Daltons, from about 1500 to about 5500 Daltons, from about 1500 to about 6000 Daltons, from about 2000 to about 2500 Daltons, from about 2000 to about 3000 Daltons, from about 2000 to about 3500 Daltons, from about 2000 to about 4000 Daltons, from about 2000 to about 4500 Daltons, from about 2000 to about 5000 Daltons, from about 2000 to about 5500 Daltons, from about 2000 to about 6000 Daltons, from about 2500 to about 3000 Daltons, from about 2500 to about 3500 Daltons, from about 2500 to about 4000 Daltons, from about 2500 to about 4500 Daltons, from about 2500 to about 5000 Daltons, from about 2500 to about 5500 Daltons, from about 2500 to about 6000 Daltons, from about 3000 to about 3500 Daltons, from about 3000 to about 4000 Daltons, from about 3000 to about 4500 Daltons, from about 3000 to about 5000 Daltons, from about 3000 to about 5500 Daltons, from about 3000 to about 6000 Daltons, from about 3500 to about 4000 Daltons, from about 3500 to about 4500 Daltons, from about 3500 to about 5000 Daltons, from about 3500 to about 5500 Daltons, from about 3500 to about 6000 Daltons, from about 4000 to about 4500 Daltons, from about 4000 to about 5000 Daltons, from about 4000 to about 5500 Daltons, from about 4000 to about 6000 Daltons, from about 4500 to about 5000 Daltons, from about 4500 to about 5500 Daltons, from about 4500 to about 6000 Daltons, from about 5000 to about 5500 Daltons, from about 5000 to about 6000 Daltons, or from about 5500 to about 6000 Daltons. In one example, the molecular weight of the PEG component is from about 851 to about 5802 Daltons. In another example, the molecular weight of the PEG component is from about 1019 to about 3775 Daltons. In another example, the molecular weight of the PEG component is from about 2749 to about 2806 Daltons. In another example, the molecular weight of the PC component is from about 509 to about 791 Daltons. In another example, the molecular weight of the PC component is from about 677 to about 791 Daltons. In another example, the molecular weight of the PC component is from about 734 to about 791 Daltons. In another example, the molecular weight of the PG component is from about 520 to about 802 Daltons. In another example, the molecular weight of the PG component is from about 688 to about 802 Daltons. In another example, the molecular weight of the PG component is from about 744 to about 802 Daltons.

The PEG component (e.g., PEG-DSPE), PG component, or PC component of the sterically stabilized liposome carrier can have a molecular weight of at least about 300 Daltons. For example, the PEG component (e.g., PEG-DSPE), PG component, or PC component of the sterically stabilized liposome carrier can have a molecular weight of at least about 300 Daltons, at least about 400 Daltons, at least about 500 Daltons, at least about 600 Daltons, at least about 700 Daltons, at least about 800 Daltons, at least about 900 Daltons, at least about 1000 Daltons, at least about 1500 Daltons, at least about 2000 Daltons, at least about 2500 Daltons, at least about 3000 Daltons, at least about 3500 Daltons, at least about 4000 Daltons, at least about 4500 Daltons, at least about 5000 Daltons, at least about 5500 Daltons, or at least about 6000 Daltons.

The head groups (phosphatidylcholine and phosphatidylglycerol) or the poly (ethylene glycol) (e.g., PEG-DSPE), may be attached to acyl groups containing from about 8 to about 24 carbon atoms. For example, the acyl group can comprise from about 8 to about 10 carbon atoms, from about 8 to about 12 carbon atoms, from about 8 to about 14 carbon atoms, from about 8 to about 16 carbon atoms, from about 8 to about 18 carbon atoms, from about 8 to about 20 carbon atoms, from about 8 to about 22 carbon atoms, from about 8 to about 24 carbon atoms, from about 10 to about 12 carbon atoms, from about 10 to about 14 carbon atoms, from about 10 to about 16 carbon atoms, from about 10 to about 18 carbon atoms, from about 10 to about 20 carbon atoms, from about 10 to about 22 carbon atoms, from about 10 to about 24 carbon atoms, from about 12 to about 14 carbon atoms, from about 12 to about 16 carbon atoms, from about 12 to about 18 carbon atoms, from about 12 to about 20 carbon atoms, from about 12 to about 22 carbon atoms, from about 12 to about 24 carbon atoms, from about 14 to about 16 carbon atoms, from about 14 to about 18 carbon atoms, from about 14 to about 20 carbon atoms, from about 14 to about 22 carbon atoms, from about 14 to about 24 carbon atoms, from about 16 to about 18 carbon atoms, from about 16 to about 20 carbon atoms, from about 16 to about 22 carbon atoms, from about 16 to about 24 carbon atoms, from about 18 to about 20 carbon atoms, from about 18 to about 22 carbon atoms, from about 18 to about 24 carbon atoms, from about 20 to about 22 carbon atoms, from about 20 to about 24 carbon atoms, or from about 22 to about 24 carbon atoms. The acyl group can comprise distearoyl, stearoyl oleoyl, stearoyl palmitoyl, dipalmitoyl, dioleoyl, palmitoyl oleoyl, or dipalmitoleoyl. The phosphatidylcholine and/or phosphatidylglycerol can be synthetically derived or derived from eggs (e.g., chicken eggs) or soy beans. The phosphatidylcholine and/or phosphatidylglycerol derived from chicken eggs can contain acyl groups having varying numbers of carbon atoms, depending on the variety and diet of the chicken that produces the eggs.

The head groups (phosphatidylcholine and phosphatidylglycerol) or the poly(ethylene glycol) (e.g., PEG-DSPE), may be attached to acyl groups containing at least about 8 carbon atoms. For example, the acyl group can comprise at least about 8, at least about 10, at least about 12, at least about 14, at least about 16, at least about 18, at least about 20, at least about 22, or at least about 24 carbon atoms.

Active Pharmaceutical Agents Such as MPL

A pharmaceutical composition described herein can comprise at least one agent, wherein the at least one agent comprises a monophosphoryl lipid A (MPL). The pharmaceutical composition can also be substantially devoid of a MPL.

In some embodiments, the pharmaceutical composition can comprise a therapeutically effective amount of at least one agent which is a therapeutic or pharmaceutical agent. In some cases, the at least one agent comprises two or more therapeutic agents for treating the same condition. In some cases, the at least one agent comprises two or more agents, wherein a first agent of the two or more agent is for treating a first condition, and wherein a second agent of the two or more agents is for treating a second condition that is different from the first condition.

In some embodiments, the at least one agent is for treating an allergy in a subject in need thereof. In some embodiments, the allergy is a food allergy, which may be a non-asthmatic food allergy. In some cases, the at least one agent is for treating an inflammatory disorder in a subject in need thereof, wherein said inflammatory disorder is not an airway inflammation. In some cases, the at least one agent is for treating eosinophilic esophagitis in a subject in need thereof. In some cases, the at least one agent is for treating tuberculosis (TB) in a subject in need thereof.

The pharmaceutical composition can comprise cholesterol. The pharmaceutical composition can also be substantially devoid of cholesterol.

The pharmaceutical composition can comprise about 0% to about 99.9% of any component of the composition, including the at least one agent, cholesterol, monophosphoryl lipid A (MPL), PEG (e.g., PEG-DSPE), PG, and PC. For example, the pharmaceutical composition can comprise about 0% to about 0.1%, about 0% to about 0.5%, about 0% to about 1%, about 0% to about 2%, about 0% to about 3%, about 0% to about 4%, about 0% to about 5%, about 0% to about 10%, about 0% to about 15%, about 0% to about 20%, about 0% to about 25%, about 0% to about 30%, about 0% to about 40%, about 0% to about 50%, about 0% to about 60%, about 0% to about 70%, about 0% to about 80%, about 0% to about 90%, about 0% to about 95%, about 0% to about 98%, about 0% to about 99%, about 0% to about 99.5%, about 0% to about 99.9%, about 0.1% to about 0.5%, about 0.1% to about 1%, about 0.1% to about 2%, about 0.1% to about 3%, about 0.1% to about 4%, about 0.1% to about 5%, about 0.1% to about 10%, about 0.1% to about 15%, about 0.1% to about 20%, about 0.1% to about 25%, about 0.1% to about 30%, about 0.1% to about 40%, about 0.1% to about 50%, about 0.1% to about 60%, about 0.1% to about 70%, about 0.1% to about 80%, about 0.1% to about 90%, about 0.1% to about 95%, about 0.1% to about 98%, about 0.1% to about 99%, about 0.1% to about 99.5%, about 0.1% to about 99.9%, about 0.5% to about 1%, about 0.5% to about 2%, about 0.5% to about 3%, about 0.5% to about 4%, about 0.5% to about 5%, about 0.5% to about 10%, about 0.5% to about 15%, about 0.5% to about 20%, about 0.5% to about 25%, about 0.5% to about 30%, about 0.5% to about 40%, about 0.5% to about 50%, about 0.5% to about 60%, about 0.5% to about 70%, about 0.5% to about 80%, about 0.5% to about 90%, about 0.5% to about 95%, about 0.5% to about 98%, about 0.5% to about 99%, about 0.5% to about 99.5%, about 0.5% to about 99.9%, about 1% to about 2%, about 1% to about 3%, about 1% to about 4%, about 1% to about 5%, about 1% to about 10%, about 1% to about 15%, about 1% to about 20%, about 1% to about 25%, about 1% to about 30%, about 1% to about 40%, about 1% to about 50%, about 1% to about 60%, about 1% to about 70%, about 1% to about 80%, about 1% to about 90%, about 1% to about 95%, about 1% to about 98%, about 1% to about 99%, about 1% to about 99.5%, about 1% to about 99.9%, about 2% to about 3%, about 2% to about 4%, about 2% to about 5%, about 2% to about 10%, about 2% to about 15%, about 2% to about 20%, about 2% to about 25%, about 2% to about 30%, about 2% to about 40%, about 2% to about 50%, about 2% to about 60%, about 2% to about 70%, about 2% to about 80%, about 2% to about 90%, about 2% to about 95%, about 2% to about 98%, about 2% to about 99%, about 2% to about 99.5%, about 2% to about 99.9%, about 3% to about 4%, about 3% to about 5%, about 3% to about 10%, about 3% to about 15%, about 3% to about 20%, about 3% to about 25%, about 3% to about 30%, about 3% to about 40%, about 3% to about 50%, about 3% to about 60%, about 3% to about 70%, about 3% to about 80%, about 3% to about 90%, about 3% to about 95%, about 3% to about 98%, about 3% to about 99%, about 3% to about 99.5%, about 3% to about 99.9%, about 4% to about 5%, about 4% to about 10%, about 4% to about 15%, about 4% to about 20%, about 4% to about 25%, about 4% to about 30%, about 4% to about 40%, about 4% to about 50%, about 4% to about 60%, about 4% to about 70%, about 4% to about 80%, about 4% to about 90%, about 4% to about 95%, about 4% to about 98%, about 4% to about 99%, about 4% to about 99.5%, about 4% to about 99.9%, about 5% to about 10%, about 5% to about 15%, about 5% to about 20%, about 5% to about 25%, about 5% to about 30%, about 5% to about 40%, about 5% to about 50%, about 5% to about 60%, about 5% to about 70%, about 5% to about 80%, about 5% to about 90%, about 5% to about 95%, about 5% to about 98%, about 5% to about 99%, about 5% to about 99.5%, about 5% to about 99.9%, about 10% to about 15%, about 10% to about 20%, about 10% to about 25%, about 10% to about 30%, about 10% to about 40%, about 10% to about 50%, about 10% to about 60%, about 10% to about 70%, about 10% to about 80%, about 10% to about 90%, about 10% to about 95%, about 10% to about 98%, about 10% to about 99%, about 10% to about 99.5%, about 10% to about 99.9%, about 15% to about 20%, about 15% to about 25%, about 15% to about 30%, about 15% to about 40%, about 15% to about 50%, about 15% to about 60%, about 15% to about 70%, about 15% to about 80%, about 15% to about 90%, about 15% to about 95%, about 15% to about 98%, about 15% to about 99%, about 15% to about 99.5%, about 15% to about 99.9%, about 20% to about 25%, about 20% to about 30%, about 20% to about 40%, about 20% to about 50%, about 20% to about 60%, about 20% to about 70%, about 20% to about 80%, about 20% to about 90%, about 20% to about 95%, about 20% to about 98%, about 20% to about 99%, about 20% to about 99.5%, about 20% to about 99.9%, about 25% to about 30%, about 25% to about 40%, about 25% to about 50%, about 25% to about 60%, about 25% to about 70%, about 25% to about 80%, about 25% to about 90%, about 25% to about 95%, about 25% to about 98%, about 25% to about 99%, about 25% to about 99.5%, about 25% to about 99.9%, about 30% to about 40%, about 30% to about 50%, about 30% to about 60%, about 30% to about 70%, about 30% to about 80%, about 30% to about 90%, about 30% to about 95%, about 30% to about 98%, about 30% to about 99%, about 30% to about 99.5%, about 30% to about 99.9%, about 40% to about 50%, about 40% to about 60%, about 40% to about 70%, about 40% to about 80%, about 40% to about 90%, about 40% to about 95%, about 40% to about 98%, about 40% to about 99%, about 40% to about 99.5%, about 40% to about 99.9%, about 50% to about 60%, about 50% to about 70%, about 50% to about 80%, about 50% to about 90%, about 50% to about 95%, about 50% to about 98%, about 50% to about 99%, about 50% to about 99.5%, about 50% to about 99.9%, about 60% to about 70%, about 60% to about 80%, about 60% to about 90%, about 60% to about 95%, about 60% to about 98%, about 60% to about 99%, about 60% to about 99.5%, about 60% to about 99.9%, about 70% to about 80%, about 70% to about 90%, about 70% to about 95%, about 70% to about 98%, about 70% to about 99%, about 70% to about 99.5%, about 70% to about 99.9%, about 80% to about 90%, about 80% to about 95%, about 80% to about 98%, about 80% to about 99%, about 80% to about 99.5%, about 80% to about 99.9%, about 90% to about 95%, about 90% to about 98%, about 90% to about 99%, about 90% to about 99.5%, about 90% to about 99.9%, about 95% to about 98%, about 95% to about 99%, about 95% to about 99.5%, about 95% to about 99.9%, about 98% to about 99%, about 98% to about 99.5%, about 98% to about 99.9%, about 99% to about 99.5%, about 99% to about 99.9%, or about 99.5% to about 99.9% of any component of the composition, including the at least one agent, cholesterol, MPL, PEG (e.g., PEG-DSPE), PG, and PC. In some cases, the pharmaceutical composition can comprise about 0% to about 99.4% of the PC. In some cases, the pharmaceutical composition can comprise about 60% to about 90% of the PC. In some cases, the pharmaceutical composition can comprise about 70% to about 80% of the PC. In some cases, the pharmaceutical composition can comprise about 0% to about 98.5% of the PC. In some cases, the pharmaceutical composition can comprise about 0.1% to about 99.4% of the PC. In some cases, the pharmaceutical composition can comprise about 0% to about 99.4% of the PG. In some cases, the pharmaceutical composition can comprise about 10% to about 40% of the PG. In some cases, the pharmaceutical composition can comprise about 20% to about 30% of the PG. In some cases, the pharmaceutical composition can comprise about 0% to about 98.5% of the PG. In some cases, the pharmaceutical composition can comprise about 0.1% to about 99.4% of the PG. In some cases, the pharmaceutical composition can comprise about 0.5% to about 10% of the PEG (e.g., PEG-DSPE). In some cases, the pharmaceutical composition can comprise about 1% to about 5% of the PEG (e.g., PEG-DSPE). In some cases, the pharmaceutical composition can comprise about 2% to about 5% of the PEG (e.g., PEG-DSPE). In some cases, the pharmaceutical composition can comprise about 0% to about 33% of the cholesterol. In some cases, the pharmaceutical composition can comprise about 0.1% to about 33% of the cholesterol. In some cases, the pharmaceutical composition can comprise about 0.1% to about 20% of the cholesterol. In some cases, the pharmaceutical composition can comprise about 0.1% to about 10% of the cholesterol. In some cases, the pharmaceutical composition can comprise about 0% to about 33% of the at least one agent. In some cases, the pharmaceutical composition can comprise about 1% to about 33% of the at least one agent.

TABLE 1

Some suitable sterically stabilized liposome carrier composition ranges useful in compositions claimed herein are shown below:

Carrier 1

| PC (mole %) | PG (mole %) | PEG-PE (mole %) |
|---|---|---|
| 0-99.4 | 0-99.4 | 0.5-10 |
| 60-90 | 10-40 | 1-5 |
| 70-80 | 20-30 | 2-5 |

Carrier 2

| PC (mole %) | PG (mole %) | PEG-PE (mole %) | CHOL (mole %) |
|---|---|---|---|
| 0-99.4 Preferred 60-90 | 0-99.4 10-40 | 0.5-10 1-5 | 0.5-33 0.5-20 |
| 70-80 | 20-30 | 2-5 | 0.5-10 |

Composition 1

| PC (mole %) | PG (mole %) | PEG-PE* (mole %) | therapeutic agents (mole %) |
|---|---|---|---|
| 0-98.5 | 0-98.5 | 0.5-10 | 1-33 |
| 60-90 | 10-40 | 1-5 | 1-33 |
| 70-80 | 20-30 | 2-5 | 1-33 |

Composition 2

| PC (mole %) | PG (mole %) | PEG-PE* (mole %) | CHOL (mole %) | therapeutic agents (mole %) |
|---|---|---|---|---|
| 0.1-99.4 | 0.1-99.4 | 0.5-10 | 0.1-33 | 1-33 |
| 60-90 | 10-40 | 1-5 | 0.1-20 | 1-33 |
| 70-80 | 20-30 | 2-5 | 0.1-10 | 1-33 |

*The molecular weight of the PEG is limited to 350.

A pharmaceutical composition described herein can comprise at least about 0.1% of any component of the composition, including the at least one agent, cholesterol, MPL, PEG (e.g., PEG-DSPE), PG, and PC. For example, the pharmaceutical composition can comprise at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, at least about 99.5%, or at least about 99.5% of any component of the composition, including the at least one agent, cholesterol, MPL, PEG (e.g., PEG-DSPE), PG, and PC.

A pharmaceutical composition described herein can comprise an effective amount of at least one agent which is a therapeutic agent, allergen, or pharmaceutical agent, and at least one of cholesterol, MPL, PEG (e.g., PEG-DSPE), PG, or PC in an oral, subcutaneous or sublingual formulation. In some cases, the ratio of the at least one agent to cholesterol, MPL, PEG, PG, or PC is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, or about 1:100. In some cases, the ratio of cholesterol to the at least one agent, MPL, PEG, PG, or PC is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1: 10, about 1:20, about 1:30, about 1:40, about 1:50, about 1:60, about 1:70, about 1:80, about 1:90, or about 1:100. In some cases, the ratio of MPL to the at least one agent, cholesterol, PEG, PG, or PC is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1: 1, about 1: 1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, or about 1:100. In some cases, the ratio of PEG to the at least one agent, cholesterol, MPL, PG, or PC is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1: 1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1: 10, about 1:20, about 1:30, about 1:40, about 1:50, about 1:60, about 1:70, about 1:80, about 1:90, or about 1:100. In some cases, the ratio of PG to the at least one agent, cholesterol, MPL, PEG, or PC is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1: 1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1: 10, about 1:20, about 1:30, about 1:40, about 1:50, about 1:60, about 1:70, about 1:80, about 1:90, or about 1:100. In some cases, the ratio of PC to the at least one agent, cholesterol, MPL, PEG, or PG is about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1: 1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, or about 1:100.

The poly (ethylene glycol)-lipid can be exchanged into biological milieu when shorter chains (e.g., palmitoyl, dimyristoyl, didodecanoyl, didecanoyl or dioctanoyl) are used. In some cases, the sterically stabilized liposome carrier can be better partitioned into the mucosal lining of a target organ after sustained shedding or sustained exchanging its poly(ethylene glycol) moiety.

The sterically stabilized liposome carrier can comprise lipids conjugated to hydrophilic steric coating molecules safe for in vivo use. For example, the hydrophilic steric coating molecule can be lipid conjugated polyoxyethylene or lipid conjugated polysorbate.

The sterically stabilized liposome carrier can comprise dipalmitoylphosphatidylcholine (DPPC). In some cases, the sterically stabilized liposome carrier can comprise dipalmitoylphosphatidylglycol (DPPG). For example, the sterically stabilized liposome carrier can comprise DPPC, DPPG, and PEG-DSPE, wherein the ratio of DPPC:DPPG:PEG-DSPE is 80:15:5. In another example, the sterically stabilized liposome carrier can comprise DPPC, DPPG, and PEG-DSPE, wherein the ratio of DPPC:DPPG:PEG-DSPE is 78:18:4.

Gel-Liquid Crystalline Phase Transition Temperature

In compositions described herein, the sterically stabilized liposome carrier can have a gel-liquid crystalline phase transition temperature in a range from about −20° C. to about 44° C. For example, the sterically stabilized liposome carrier can have a gel-liquid crystalline phase transition temperature in a range from about −20° C. to about −10° C., from about −20° C. to about 0° C., from about −20° C. to about 10° C., from about −20° C. to about 20° C., from about −20° C. to about 30° C., from about −20° C. to about 37° C. from about −20° C. to about 40° C., from about −20° C. to about 42° C., from about −20° C. to about 44° C., from about −10° C. to about 0° C., from about −10° C. to about 10° C., from about −10° C. to about 20° C., from about −10° C. to about 30° C., from about −10° C. to about 37° C., from about −10° C. to about 40° C., from about −10° C. to about 42° C., from about −10° C. to about 44° C., from about 0° C. to about 10° C., from about 0° C. to about 20° C., from about 0° C. to about 30° C., from about 0° C. to about 37° C., from about 0° C. to about 40° C., from about 0° C. to about 42° C., from about 0° C. to about 44° C., from about 10° C. to about 20° C., from about 10° C. to about 30° C. from about 10° C. to about 37° C., from about 10° C. to about 40° C., from about 10° C. to about 42° C., from about 10° C. to about 44° C., from about 20° C. to about 30° C., from about 20° C. to about 37° C., from about 20° C. to about 40° C., from about 20° C. to about 42° C., from about 20° C. to about 44° C., from about 30° C. to about 37° C., from about 30° C. to about 40° C., from about 30° C. to about 42° C., from about 30° C. to about 44° C., from about 37° C. to about 40° C., from about 37° C. to about 42° C., from about 37° C. to about 44° C., from about 40° C. to about 42° C., from about 40° C. to about 44° C., or from about 42° C. to about 44° C. In some cases, the sterically stabilized liposome carrier can have a gel-liquid crystalline phase transition temperature in a range from about −10° C. to about 42° C. In some cases, the composition is substantially devoid of cholesterol. In some cases, the composition comprises an amount of cholesterol, wherein the amount of cholesterol is sufficient for the transition range of the sterically stabilized liposome carrier containing cholesterol to be broadened compared to that of sterically stabilized liposome carriers substantially devoid of cholesterol. In some cases, are provided stabilized liposome carriers with sufficient cholesterol to enable a relatively high transition temperature (e.g., in the gel phase at 37° C.) to have a substantial portion of the membrane in the fluid or liquid crystalline phase at body temperature.

The sterically stabilized liposome carrier can have a gel-liquid crystalline phase transition temperature of at least about −20° C. For example, the sterically stabilized liposome carrier can have a gel-liquid crystalline phase transition temperature of at least about −20° C., at least about −10° C., at least about 0° C., at least about 10° C., at least about 20° C., at least about 30° C., at least about 37° C., at least about 40° C., at least about 42° C., or at least about 44° C.

Vesicle Sizes

In certain embodiments, pharmaceutical compositions for oral, subcutaneous or sublingual administration as described herein, can comprise vesicles (e.g., unilamellar or multilamellar) having an average diameter of about 0.01 to about 50 microns. For example, the pharmaceutical composition can comprise vesicles (e.g., unilamellar or multilamellar) having an average diameter of about 0.01 to about 0.02 microns, about 0.01 to about 0.05 microns, about 0.01 to about 0.1 microns, about 0.01 to about 0.5 microns, about 0.01 to about 1 microns, about 0.01 to about 1.5 microns, about 0.01 to about 2 microns, about 0.01 to about 2.5 microns, about 0.01 to about 3 microns, about 0.01 to about 4 microns, about 0.01 to about 5 microns, about 0.01 to about 10 microns, about 0.01 to about 20 microns, about 0.01 to about 30 microns, about 0.01 to about 40 microns, about 0.01 to about 50 microns, about 0.02 to about 0.05 microns, about 0.02 to about 0.1 microns, about 0.02 to about 0.5 microns, about 0.02 to about 1 microns, about 0.02 to about 1.5 microns, about 0.02 to about 2 microns, about 0.02 to about 2.5 microns, about 0.02 to about 3 microns, about 0.02 to about 4 microns, about 0.02 to about 5 microns, about 0.02 to about 10 microns, about 0.02 to about 20 microns, about 0.02 to about 30 microns, about 0.02 to about 40 microns, about 0.02 to about 50 microns, about 0.05 to about 0.1 microns, about 0.05 to about 0.5 microns, about 0.05 to about 1 microns, about 0.05 to about 1.5 microns, about 0.05 to about 2 microns, about 0.05 to about 2.5 microns, about 0.05 to about 3 microns, about 0.05 to about 4 microns, about 0.05 to about 5 microns, about 0.05 to about 10 microns, about 0.05 to about 20 microns, about 0.05 to about 30 microns, about 0.05 to about 40 microns, about 0.05 to about 50 microns, about 0.1 to about 0.5 microns, about 0.1 to about 1 microns, about 0.1 to about 1.5 microns, about 0.1 to about 2 microns, about 0.1 to about 2.5 microns, about 0.1 to about 3 microns, about 0.1 to about 4 microns, about 0.1 to about 5 microns, about 0.1 to about 10 microns, about 0.1 to about 20 microns, about 0.1 to about 30 microns, about 0.1 to about 40 microns, about 0.1 to about 50 microns, about 0.5 to about 1 microns, about 0.5 to about 1.5 microns, about 0.5 to about 2 microns, about 0.5 to about 2.5 microns, about 0.5 to about 3 microns, about 0.5 to about 4 microns, about 0.5 to about 5 microns, about 0.5 to about 10 microns, about 0.5 to about 20 microns, about 0.5 to about 30 microns, about 0.5 to about 40 microns, about 0.5 to about 50 microns, about 1 to about 1.5 microns, about 1 to about 2 microns, about 1 to about 2.5 microns, about 1 to about 3 microns, about 1 to about 4 microns, about 1 to about 5 microns, about 1 to about 10 microns, about 1 to about 20 microns, about 1 to about 30 microns, about 1 to about 40 microns, about 1 to about 50 microns, about 1.5 to about 2 microns, about 1.5 to about 2.5 microns, about 1.5 to about 3 microns, about 1.5 to about 4 microns, about 1.5 to about 5 microns, about 1.5 to about 10 microns, about 1.5 to about 20 microns, about 1.5 to about 30 microns, about 1.5 to about 40 microns, about 1.5 to about 50 microns, about 2 to about 2.5 microns, about 2 to about 3 microns, about 2 to about 4 microns, about 2 to about 5 microns, about 2 to about 10 microns, about 2 to about 20 microns, about 2 to about 30 microns, about 2 to about 40 microns, about 2 to about 50 microns, about 2.5 to about 3 microns, about 2.5 to about 4 microns, about 2.5 to about 5 microns, about 2.5 to about 10 microns, about 2.5 to about 20 microns, about 2.5 to about 30 microns, about 2.5 to about 40 microns, about 2.5 to about 50 microns, about 3 to about 4 microns, about 3 to about 5 microns, about 3 to about 10 microns, about 3 to about 20 microns, about 3 to about 30 microns, about 3 to about 40 microns, about 3 to about 50 microns, about 4 to about 5 microns, about 4 to about 10 microns, about 4 to about 20 microns, about 4 to about 30 microns, about 4 to about 40 microns, about 4 to about 50 microns, about 5 to about 10 microns, about 5 to about 20 microns, about 5 to about 30 microns, about 5 to about 40 microns, about 5 to about 50 microns, about 10 to about 20 microns, about 10 to about 30 microns, about 10 to about 40 microns, about 10 to about 50 microns, about 20 to about 30 microns, about 20 to about 40 microns, about 20 to about 50 microns, about 30 to about 40 microns, about 30 to about 50 microns, or about 40 to about 50 microns. In some cases, the pharmaceutical composition can comprise vesicles (e.g., unilamellar or multilamellar) having an average diameter of about 0.02 to about 2.5 microns. In some cases, the pharmaceutical composition can comprise vesicles (e.g., unilamellar or multilamellar) having an average diameter of about 0.05 to about 5 microns. In some cases, the desired sizes of vesicles can be obtained from extrusion of the pharmaceutical composition through polycarbonate membranes having pores of selected sizes, e.g. from about 0.05 to about 5 microns.

In certain embodiments, pharmaceutical compositions for oral, subcutaneous or sublingual administration as described herein can comprise vesicles (e.g., unilamellar or multilamellar) having an average diameter of at least about 0.01 microns. For example, the pharmaceutical composition can comprise vesicles (e.g., unilamellar or multilamellar) having an average diameter of at least about 0.01 microns, at least about 0.02 microns, at least about 0.05 microns, at least about 0.1 microns, at least about 0.5 microns, at least about 1 microns, at least about 1.5 microns, at least about 2 microns, at least about 2.5 microns, at least about 3 microns, at least about 4 microns, at least about 5 microns, at least about 10 microns, at least about 20 microns, at least about 30 microns, at least about 40 microns, or at least about 50 microns.

Antibodies

In certain embodiments, pharmaceutical compositions for oral, subcutaneous or sublingual administration as described herein can comprise at least one agent, wherein the at least one agent comprises an antibody, derivative or fragment thereof. In some cases, the antibody is an anti-IgE antibody, derivative or fragment thereof. In some embodiments, the anti-IgE antibody can be, for example, recombinant, fully human, humanized, camelid, diabody or a chimeric antibody.

In some embodiments is provided a pharmaceutical composition for oral, subcutaneous or sublingual administration as described herein, comprising an antibody and sterically stabilized liposome carrier described herein, wherein the antibody can be an antibody against a molecule or target recognized to have a role in modulating an allergic response to food in a subject, e.g., in a human. In some embodiments, the pharmaceutical composition can be orally co-administered or sequentially administered with an allergen. In some embodiments, an allergen can be included in the pharmaceutical composition. For example, an anti-IgE antibody can be loaded into a sterically stabilized liposome carrier described herein along with a peanut derivative or peanut extract such as peanut protein, peanut powder or peanut butter for administration as part of an allergy treatment. The administration can be subcutaneous, sublingual, or oral, and in some embodiments provided about once a week. The pharmaceutical composition can also be substantially devoid of an antibody.

Locations of Agents and/or Allergens in Sterically Stabilized Liposome Carriers

As shown in FIG. 1, liposomes can have at least a membrane portion and an interior portion. A sterically stabilized liposome carrier includes an anti-IgE antibody (105) located in a membrane of the sterically stabilized liposome carrier and an allergen (110) located in a hydrophilic core (interior portion) of the sterically stabilized liposome.

The interior portion can be largely aqueous, having a different environment from the phospholipid bilayer of the membrane portion. Further, in some liposomes, multilamellar liposomes (not shown), there can be multiple membranes per liposome with interior portions between the membranes.

In some cases, one or more agent can be loaded into separate portions of the liposomes. For example, MPL can be loaded into (e.g., embedded in) the membrane portion, while the therapeutic agent or allergen is located in the interior portion. In another example, the therapeutic agent can be loaded in both the interior and membrane portions of the liposome. A wide variety of combinations are possible, according to the thermodynamics and kinetics of the partitioning of various agents between the interior (aqueous) and membrane (hydrophobic/amphipathic) portions of the liposome, as well as on the manner of formation of liposome and loading of the therapeutic agent. In some cases, MPL is loaded into the membrane. In some cases, an anti-IgE antibody or fragment or derivative thereof is loaded into the membrane portion of the liposome, while an allergen or derivative thereof (e.g., peanut protein, peanut powder, peanut butter) is loaded into the interior portion of the liposome. In some cases, anti-IgE antibody or fragment or derivative thereof is placed (at least in part) in the interior of the liposome, permitting a controlled release of the antibody from the liposome. In some cases, a drug or therapeutic or pharmaceutical agent (e.g., steroid) is added to the liposome, in addition to the protein (e.g., peanut protein). Compositions comprising the sterically stabilized liposome carrier described herein can then be administered subcutaneously, sublingually, or orally to a subject in need of thereof.

In some cases, one or more pharmaceutical or therapeutic agent is not loaded exclusively into a single liposome compartment, but rather can be predominately loaded into the compartment, e.g., more than about 50%, 55%, 60%, 65%, 70%, 75%, 80%, 85%, 90%, 95%, or 99% of the one or more agent is loaded into a specified portion (interior or membrane) of the liposome.

A sterically stabilized liposome carrier described herein can comprise a population of individual liposomes, such that the carrier can be said to have an interior portion (meaning, for example, the collective interior portions of the constituent liposomes) and a membrane portion (meaning, for example, the collective membrane portions of the constituent liposomes).

The pharmaceutical composition can comprise at least one agent, wherein said agent is at least one of a therapeutic agent and an allergen, wherein about 1% to about 99% of the at least one agent is in a membrane or internal portion of the liposome carrier. For example, about 1% to about 2%, about 1% to about 3%, about 1% to about 4%, about 1% to about 5%, about 1% to about 10%, about 1% to about 15%, about 1% to about 20%, about 1% to about 25%, about 1% to about 30%, about 1% to about 40%, about 1% to about 50%, about 1% to about 60%, about 1% to about 70%, about 1% to about 80%, about 1% to about 90%, about 1% to about 95%, about 1% to about 98%, about 1% to about 99%, about 2% to about 3%, about 2% to about 4%, about 2% to about 5%, about 2% to about 10%, about 2% to about 15%, about 2% to about 20%, about 2% to about 25%, about 2% to about 30%, about 2% to about 40%, about 2% to about 50%, about 2% to about 60%, about 2% to about 70%, about 2% to about 80%, about 2% to about 90%, about 2% to about 95%, about 2% to about 98%, about 2% to about 99%, about 3% to about 4%, about 3% to about 5%, about 3% to about 10%, about 3% to about 15%, about 3% to about 20%, about 3% to about 25%, about 3% to about 30%, about 3% to about 40%, about 3% to about 50%, about 3% to about 60%, about 3% to about 70%, about 3% to about 80%, about 3% to about 90%, about 3% to about 95%, about 3% to about 98%, about 3% to about 99%, about 4% to about 5%, about 4% to about 10%, about 4% to about 15%, about 4% to about 20%, about 4% to about 25%, about 4% to about 30%, about 4% to about 40%, about 4% to about 50%, about 4% to about 60%, about 4% to about 70%, about 4% to about 80%, about 4% to about 90%, about 4% to about 95%, about 4% to about 98%, about 4% to about 99%, about 5% to about 10%, about 5% to about 15%, about 5% to about 20%, about 5% to about 25%, about 5% to about 30%, about 5% to about 40%, about 5% to about 50%, about 5% to about 60%, about 5% to about 70%, about 5% to about 80%, about 5% to about 90%, about 5% to about 95%, about 5% to about 98%, about 5% to about 99%, about 10% to about 15%, about 10% to about 20%, about 10% to about 25%, about 10% to about 30%, about 10% to about 40%, about 10% to about 50%, about 10% to about 60%, about 10% to about 70%, about 10% to about 80%, about 10% to about 90%, about 10% to about 95%, about 10% to about 98%, about 10% to about 99%, about 15% to about 20%, about 15% to about 25%, about 15% to about 30%, about 15% to about 40%, about 15% to about 50%, about 15% to about 60%, about 15% to about 70%, about 15% to about 80%, about 15% to about 90%, about 15% to about 95%, about 15% to about 98%, about 15% to about 99%, about 20% to about 25%, about 20% to about 30%, about 20% to about 40%, about 20% to about 50%, about 20% to about 60%, about 20% to about 70%, about 20% to about 80%, about 20% to about 90%, about 20% to about 95%, about 20% to about 98%, about 20% to about 99%, about 25% to about 30%, about 25% to about 40%, about 25% to about 50%, about 25% to about 60%, about 25% to about 70%, about 25% to about 80%, about 25% to about 90%, about 25% to about 95%, about 25% to about 98%, about 25% to about 99%, about 30% to about 40%, about 30% to about 50%, about 30% to about 60%, about 30% to about 70%, about 30% to about 80%, about 30% to about 90%, about 30% to about 95%, about 30% to about 98%, about 30% to about 99%, about 40% to about 50%, about 40% to about 60%, about 40% to about 70%, about 40% to about 80%, about 40% to about 90%, about 40% to about 95%, about 40% to about 98%, about 40% to about 99%, about 50% to about 60%, about 50% to about 70%, about 50% to about 80%, about 50% to about 90%, about 50% to about 95%, about 50% to about 98%, about 50% to about 99%, about 60% to about 70%, about 60% to about 80%, about 60% to about 90%, about 60% to about 95%, about 60% to about 98%, about 60% to about 99%, about 70% to about 80%, about 70% to about 90%, about 70% to about 95%, about 70% to about 98%, about 70% to about 99%, about 80% to about 90%, about 80% to about 95%, about 80% to about 98%, about 80% to about 99%, about 90% to about 95%, about 90% to about 98%, about 90% to about 99%, about 95% to about 98%, about 95% to about 99%, or about 98% to about 99% of the at least one agent is in a membrane or internal portion of the liposome carrier.

The pharmaceutical composition can comprise at least one agent, wherein at least about 1% of the at least one agent is in a membrane or internal portion of the liposome carrier. For example, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the at least one agent is in a membrane or internal portion of the liposome carrier.

Controlled Release of Agents From Liposomes by Tuning pH-Stability

The release of the one or more agents from the sterically stabilized liposome carrier can be controlled by tuning pH-stability to adjust to various body compartments with different pH profiles. Therefore, the sterically stabilized liposome carrier can be stable in one pH range and not in another. For example, the sterically stabilized liposome carrier can be selected to be stable in the stomach but not in the small intestine, or vice versa, thereby. For example, the sterically stabilized liposome carrier can be tuned to be stable above about pH 3, 4, 5, 6, 7, 8, 9, and 10; or below about pH 10, 9, 8, 7, 6, 5, 4, or 3. In some cases, two populations of sterically stabilized liposome carriers can be used: a first population of sterically stabilized liposome carrier is stable in acid and passes through the stomach with contents inside, but which is not stable in the small intestine, where its liposomal contents are released: a second population is not stable in the stomach and releases its contents there. In this manner, the pharmaceutical composition described herein can be used to control the release of multiple agents in different body compartments. In some cases, the pharmaceutical composition and/or the sterically stabilized liposome carrier can comprise cholesteryl hemisuccinate. In some cases, the pharmaceutical composition and/or the sterically stabilized liposome carrier can be substantially devoid of cholesteryl hemisuccinate.

A pH sensitive component of the pharmaceutical composition and/or the sterically stabilized liposome carrier can comprise a phospholipid, an acylated amino acid, a fatty acid, a cholesterol or cholesterol derivative, a double chain amphiphile, or any combination thereof. For example, the pH sensitive component can be N-palmitoyl homocysteine (PHC).

The pharmaceutical composition and/or the sterically stabilized liposome carrier can be stable or can release its content at about pH 1 to about pH 14. For example, the pharmaceutical composition and/or the sterically stabilized liposome carrier can be stable at about pH 1 to about pH 2, about pH 1 to about pH 3, about pH 1 to about pH 4, about pH 1 to about pH 5, about pH 1 to about pH 6, about pH 1 to about pH 7, about pH 1 to about pH 8, about pH 1 to about pH 9, about pH 1 to about pH 10, about pH 1 to about pH 11, about pH 1 to about pH 12, about pH 1 to about pH 13, about pH 1 to about pH 14, about pH 2 to about pH 3, about pH 2 to about pH 4, about pH 2 to about pH 5, about pH 2 to about pH 6, about pH 2 to about pH 7, about pH 2 to about pH 8, about pH 2 to about pH 9, about pH 2 to about pH 10, about pH 2 to about pH 11, about pH 2 to about pH 12, about pH 2 to about pH 13, about pH 2 to about pH 14, about pH 3 to about pH 4, about pH 3 to about pH 5, about pH 3 to about pH 6, about pH 3 to about pH 7, about pH 3 to about pH 8, about pH 3 to about pH 9, about pH 3 to about pH 10, about pH 3 to about pH 11, about pH 3 to about pH 12, about pH 3 to about pH 13, about pH 3 to about pH 14, about pH 4 to about pH 5, about pH 4 to about pH 6, about pH 4 to about pH 7, about pH 4 to about pH 8, about pH 4 to about pH 9, about pH 4 to about pH 10, about pH 4 to about pH 11, about pH 4 to about pH 12, about pH 4 to about pH 13, about pH 4 to about pH 14, about pH 5 to about pH 6, about pH 5 to about pH 7, about pH 5 to about pH 8, about pH 5 to about pH 9, about pH 5 to about pH 10, about pH 5 to about pH 11, about pH 5 to about pH 12, about pH 5 to about pH 13, about pH 5 to about pH 14, about pH 6 to about pH 7, about pH 6 to about pH 8, about pH 6 to about pH 9, about pH 6 to about pH 10, about pH 6 to about pH 11, about pH 6 to about pH 12, about pH 6 to about pH 13, about pH 6 to about pH 14, about pH 7 to about pH 8, about pH 7 to about pH 9, about pH 7 to about pH 10, about pH 7 to about pH 11, about pH 7 to about pH 12, about pH 7 to about pH 13, about pH 7 to about pH 14, about pH 8 to about pH 9, about pH 8 to about pH 10, about pH 8 to about pH 11, about pH 8 to about pH 12, about pH 8 to about pH 13, about pH 8 to about pH 14, about pH 9 to about pH 10, about pH 9 to about pH 11, about pH 9 to about pH 12, about pH 9 to about pH 13, about pH 9 to about pH 14, about pH 10 to about pH 11, about pH 10 to about pH 12, about pH 10 to about pH 13, about pH 10 to about pH 14, about pH 11 to about pH 12, about pH 11 to about pH 13, about pH 11 to about pH 14, about pH 12 to about pH 13, about pH 12 to about pH 14, or about pH 13 to about pH 14. In some cases, the at least one agent can be released from the liposome carrier in a pH sensitive manner, for example, the at least one agent can be released from the liposome carrier in one of the above pH ranges. In some cases, the at least one agent can be released from the liposome carrier in a pH independent manner.

The pharmaceutical composition and/or the sterically stabilized liposome carrier can remain stable in the presence of serum and/or in the extra-cellular environment. In some cases, the stability of the sterically stabilized liposome carrier in combination with the encapsulated therapeutic agent is more pronounced than currently available drug therapies. In some cases, the stability of the sterically stabilized liposome carrier can allow a therapeutic agent, such as a corticosteroid, to be administered only once every one to two weeks. The dosage used in these treatments is typically the same or similar to that used on a daily basis. The therapeutic agent may thus be administered at two, three, four, five, six or seven days or longer intervals. In some instances, the effective life may be up to two weeks or longer. The term "effective life" as used herein means a period during which the therapeutic agent effect is continued.

Multiple Populations of Liposomes

In some embodiments, more than one population of liposome (e.g., differing in one or more characteristics, such as agents contained, phospholipid composition, presence absence of anti-IgE antibody, cholesterol, or steroid) are administered to a subject in need thereof.

Formulations

The pharmaceutical compositions can be formulated as a formulation for oral, subcutaneous, sublingual or buccal administration. The formulation can comprise nontoxic therapeutically acceptable carriers, adjuvants, and/or vehicles as desired. The formulation can be in dosage unit as desired.

Formulation of therapeutic agents is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The pharmaceutical compositions may be administered per se or in the form of a formulation wherein the active compound(s) is in admixture or mixture with one or more therapeutically acceptable carriers, excipients or diluents. Pharmaceutical compositions may be formulated in conventional manner using one or more therapeutically acceptable carriers comprising excipients and auxiliaries which facilitate processing of the active compounds into preparations which can be used therapeutically. Proper formulation is dependent upon the route of administration chosen.

Compositions described herein can be provided as lyophiles. A lyophilized formulation described here in can be further formulated for oral delivery for instance, in tablet or capsule form. Lyophile compositions described herein can be deposited on a filter paper for oral delivery to a subject. Specific lyophile compositions described herein can comprise additional excipients or stabilizers which in some cases can be useful to stabilize the liposomes in lyophilized form. In some embodiments, lyophile compositions described herein can comprise a sugar, in some cases in an amount sufficient to stabilize the liposomes in lyophilized form. In some embodiments, the sugar can selected from the group consisting of trehalose, glucose, sucrose, maltose, galactose, fructose, and arabinose. In specific embodiments are provided compositions described herein, further comprising an amount of trehalose.

In some cases, lyophile composition described herein can be stable for a period of up to about 3 months. In some cases, lyophile compositions described herein can be stable for a period of up to about 6 months, about 9 months, about 1 year, about 1.5 years, about 2 years, about 2.5 years, about 3 years, about 3.5 years, about 4 years, about 4.5 years or about 5 years. In some cases, after about 6 months, the lyophile composition retains about 100% efficacy. In some cases, after 6 months, the lyophile composition retains about 99%, 97%, 95%, 90%, 85%, 80%, 75% or 70% efficacy.

In some cases, a lyophile compositions described herein is reconstituted prior to administration. In some cases, the administration is oral, subcutaneous or sublingual. In some cases, the administration is intranasal. In some cases, the composition is reconstituted with an appropriate diluent. In some embodiments, the diluent comprises a solvent or co-solvent selected from tert-butyl alcohol, n-butanol, ethanol, iso-propyl alcohol, dimethyl sulfone, chlorobutanol, Sterile Water for Injection, 0.9% sodium chloride solution, 5% dextrose solution, or mixtures thereof. In some cases, the composition is reconstituted with an aqueous diluent. In some embodiments, the aqueous diluent is selected from the group consisting of: distilled water, deionized water; sterile water; bacteriostatic water; and normal saline.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Therapeutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicon dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The compounds may be complexed with other agents as part of their being therapeutically formulated. The pharmaceutical compositions may take the form of, for example, tablets or capsules prepared by conventional means with therapeutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations (e.g. for oral administration) prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

Delayed release and extended release compositions (e.g., for buccal administration) can be prepared. The delayed release/extended release pharmaceutical compositions can be obtained by complexing therapeutic agent with a therapeutically acceptable ion-exchange resin and coating such complexes. The formulations are coated with a substance that will act as a barrier to control the diffusion of the therapeutic agent from its core complex into the gastrointestinal fluids. Optionally, the formulation is coated with a film of a polymer which is insoluble in the acid environment of the stomach, and soluble in the basic environment of lower GI tract in order to obtain a final dosage form that releases less than 10% of the therapeutic agent dose within the stomach.

In addition, combinations of immediate release compositions and delayed release/extended release compositions may be formulated together.

Lyophilization Methods

Lyophilization is the technical name for a process often referred to as "freeze-drying." In this process, an aqueous mixture or suspension is frozen into a solid, then it is generally subjected to a vacuum for a substantial period of time. The vacuum causes the water molecules to sublimate.

The methods described herein include the step of lyophilizing the composition comprising a sterically stabilized liposome carrier as described herein. In one embodiment, lyophilization occurs after sterilization. In one embodiment, during the lyophilization process, the solvent system used, such as by way of example only, tert-butyl alcohol and Sterile Water for Injection is substantially removed by sublimation. In another embodiment, less than about 5% residual solvent remains after lyophilization; in other embodiments, less than about 3% remains; in yet other embodiments, less than about 2% remains; in further embodiments, less than about 1% or about 0.1% remains.

In one embodiment, the lyophilization process comprises the steps of (1) placing the sample to be lyophilized (composition comprising sterically stabilized liposome carrier and optionally an active agent) in a suitable vial and placing the vial into a lyophilization chamber and lowering the shelf temperature to about −30° C. to about −50° C. at atmospheric pressure: (2) holding the shelf temperature at the temperature range described above until the temperature of the sample is about −30° C. to about −50° C.; (3) raising the temperature to about −10° C. to about −20° C. to anneal the lyophile for about 1 to 2 hours; (4) lowering the shelf temperature to about −30° C. to about −50° C. and reducing the pressure of the system to about 50 mTorr to about 100 mTorr; and holding until sublimation of the solvent system is substantially complete. The temperature of the product should be below about −25° C. to about −28° C. to avoid cake collapse; (5) increasing the temperature to about 30° C. to about 50° C.; and (6) allowing the samples to reach a temperature of about 20° C. to about 30° C. for an amount of time to remove bound water or solvent levels; (7) backfilling vials with nitrogen or appropriate gas after which the vials are aseptically sealed. Table 7 describes, in one embodiment, the lyophilization cycle for lyophilizing a bulk solution comprising fluticasone or salmeterol or their pharmaceutically acceptable salts or a combination thereof. In one embodiment, the process requires a step-wise lowering or increasing of the temperature of the system, such as, at a rate of 0.5° C. per minute up to about 1° C. per minute to ensure proper and substantially complete sublimation. The lyophilization step provides a composition comprising sterically stabilized liposome carrier and optionally an active agent, such as, for example, an allergen or a steroid or a combination thereof, that can be stored at room temperature for extended periods of time. Additionally, the lyophilized compositions (also referred to as lyophiles) described herein are stable for a period of at least 4 weeks at a temperature of about 0° C. to about 50° C. In some embodiments, the lyophilized compositions are stable from at least about 3 months to at least about 5 years at a temperature of about 0° C. to about 50° C. In certain embodiments, the lyophilized compositions are stable for a period of at least about 4 months to at least about 4 years at a temperature of about 0° C. to about 50° C. In still further or additional embodiments, the lyophilized compositions are stable for a period of at least about 6 months to at least about 2 years at a temperature of about 0° C. to about 50° C. In some embodiments, the lyophilized compositions are stable for at least about 3 months, at least about 6 months, at least about 1 year, at least about 2 years, at least about 3 years, at least about 4 years, or at least about 5 years at a temperature of about 0° C. to about 50° C. In other embodiments, the lyophiles described herein are in the form of a cake or free flowing powder. In other embodiment, the lyophilized composition is a cake.

Reconstitution

In some embodiments, the lyophiles described herein readily reconstitute once contacted with a sufficient amount of a pharmaceutically acceptable carrier or diluent. For example, in some embodiments, the lyophile is mixed in the vial it is contained in, e.g., shaken for about 1 to about 3 minutes, with a pharmaceutically acceptable carrier, such as, Sterile Water for Injection, 0.9% sodium chloride solution, or 5% dextrose solution to provide a reconstituted composition suitable for subcutaneous injection. In one embodiment, the lyophile is reconstituted in a relatively short period of time, such as for example, less than 1 minute, less than 30 seconds, and in other embodiments, about 20 seconds. In certain embodiments, the lyophiles reconstitute in a time of less than 2, 3, 4, or 5 minutes. These short reconstitution times provide an advantage in that the therapeutic agent has not decomposed from exposure in a solution for an extended period of time prior to administration. In one embodiment, the reconstituted composition is suitable for subcutaneous administration, such as for example, subcutaneous injection. In another embodiment, the reconstituted form is a non-suspension. In a further embodiment, the reconstituted form is a clear solution and remains substantially clear prior to administration.

A feature of the subject matter described herein is a lyophilized composition is formulated with a minimal amount of trehalose, that is manufactured as a lyophile, and that is amenable to full reconstitution with a carrier or diluents in a short period of time.

Route of Administration

Compositions described herein can be administered orally, sublingually, buccally, subcutaneously, intramuscularly, rectally, intradermally, transdermally, by inhalation, or topically. In some cases, the compositions can be administered via subcutaneous injection, or infusion techniques. In some cases, the pharmaceutical composition is suitable for subcutaneous, sublingual, or oral administration, but not inhalation or pulmonary delivery. In some cases, the composition is administered orally. In some cases, the composition is administered subcutaneously. In some cases, the composition is administered sublingually. In some cases, the composition is administered buccally.

Schedule of Administration

Provided are pharmaceutical compositions suitable for sustained slow release of an active agent upon oral, sublingual or subcutaneous administration to a subject. The pharmaceutical composition and/or sterically stabilized liposome carrier can be administered to a subject in need thereof three times daily, twice daily, once daily, seven times weekly, six times weekly, five times weekly, four times weekly, three times weekly, twice weekly, once weekly, every other week, or monthly.

The pharmaceutical composition and/or sterically stabilized liposome carrier can be administered to a subject in need thereof with a dosage schedule less frequent. In some cases, the pharmaceutical composition is administered subcutaneously, sublingually, or orally. In some cases, the pharmaceutical composition and/or sterically stabilized liposome carrier can be administered to a subject in need thereof with a dosage schedule about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% less frequent than a comparable composition with a different carrier (e.g., conventional carrier that is not a sterically stabilized liposome carrier) or a comparable composition with different route of administration (e.g., IV).

Compositions and Methods for Treating an Allergy

Disclosed herein are methods and compositions for treating an allergy or inducing tolerance to an allergen, comprising administering a pharmaceutical composition described herein to a subject in need thereof. In specific embodiments, the allergy is a food allergy, for instance an IgE mediated food allergy. In some embodiments, the allergy does not result in an airway inflammation. The pharmaceutical composition can comprise a therapeutically effective amount of at least one agent for treating an allergy or inducing tolerance to an allergen. In some cases, the allergy is not allergic asthma. In some cases, administration of a composition described herein to a subject in need thereof, can result in decreasing inflammation, anaphylaxis, gastrointestinal inflammation/reaction, skin rashes/urticaria/angioedema, or any combination thereof. In some embodiments, the subject is at risk for developing a food allergy (e.g., IgE mediated food allergy). For example, the subject has a family history of developing a food allergy (e.g., IgE mediated food allergy). In some embodiments, the subject is at risk for developing a gastrointestinal allergy. For example, the subject has a family history of developing a gastrointestinal allergy. In some embodiments, the subject has an elevated antibody level (e.g., IgE) to an allergen (e.g., food allergen). The methods and compositions described herein can be used to reset the IgE antibody production in the subject to the allergen, and thereby can allow an individual to tolerate exposure to that allergen without a reaction.

In certain embodiments is provided a composition suitable for oral, sublingual or subcutaneous administration comprising at least one agent at least one agent for treating an allergy or inducing tolerance to an allergen, and a sterically stabilized liposome carrier as described herein. In some embodiments, the at least one agent can comprise an allergen. Without limitation, an allergen can be included in the liposome, optionally in addition to any other contents, such as those listed above. It should be appreciated that a wide variety of food allergens can be used. Examples of allergens are substances capable of inducing an allergic response in a mammal, e.g., a human. Examples of allergens include for instance, proteins (whole or fragments), peptides, polypeptides, recombinant peptides. Some allergens can be derived from, or related to food substances (e.g., peanut, tree nut, egg, shellfish, soy, milk, gluten). Still other allergens come from medicines, including small molecule medicines, e.g., penicillin, sulfa drugs. Yet other allergens are contact allergens, e.g., poison ivy (urushiol). Peanut allergens that can be used in compositions for oral, subcutaneous or sublingual administration as described herein, include, for instance, without limitation Ara h 1, Ara h2, Ara h3, and Ara h8. Additional allergen that can be provided as part of, or in conjunction with a composition suitable for oral, sublingual or subcutaneous administration described herein, are listed in the tables below.

TABLE 2

Major Class II Food Allergens, including the following:

| Plant Allergen | Protein | Food | Food Allergen |
|---|---|---|---|
| Latex-fruit cross reactivity | Class I chitinases | Avocado, chestnut, banana | |
| | Thaumatin-like | Cherry | Pru A2 |
| | | Apple | Mal d2 |
| Birch | Bet vl homologues = pathogen-related proteins 10 | Apple | Mal d 1 |
| | | Cherry | Pru a 1 |
| | | Pear | Pyr a 1 |
| | | Celery | Api g 1 |
| | | Carrot | Dau c 1 |
| | | Potato | |
| Celery-mugwort spice syndrome | Bet v2 homologues = Profilin | Latex | Hev b 8 |
| | | Celery | Api g 4 |
| | | Potato | |
| | | Cherry | Pru av 4 |
| | | Pear | Pyr c 4 |
| | | Peanut | Ara h 5 |
| | | Soybean | Gly m 3 |
| | | Apple, tomato, and carrot | |
| | Lipid-transfer proteins | Peach | Pru p |
| | | Apple | Mal d3 |
| | | Soy | |
| Seed Storage Proteins | 2S albumin | Mustard | Sin a 1 |
| | | English walnut | Jug r 1 |
| | | Rapeseed and Brazil nut | |
| | Vicilin | Peanut | Ara h 1 |
| | | Walnut | Jug r 1 |
| | Conglutin | Peanut | Ara h2 |
| | Glycinin | Peanut | Ara h3 |
| | | Soy | |
| | β-Glycinin | Soy | |

TABLE 3

Major Class 1 Food Allergens, including the following:

| Foods | Examples of Proteins | Examples of Food Allergens |
|---|---|---|
| Cow's milk | Caseins | Bos d 8 |
| | αs1-Casein | |
| | αs2-Casein | |
| | β-Casein | |
| | κ-Casein | |
| | Whey | |
| | β-Lactoglobulin | Bos d 5 |
| | α-Lactalbumin Bos d 4 | Bos d 4 |
| | Serum albumin | Bos d 6 |
| Chicken egg white | Ovalbumin | Gal d 1 |
| | Ovomucoid | Gal d 2 |
| | Ovotransferrin | Gal d 3 |
| Wheat | Globulin | |
| | Glutenin | |
| Peanut | Vicilin | Ara h 1 |
| | Conglutin | Ara h 2 |
| | Glycinin | Ara h 3 |
| Soybean | Glycinin G1 acidic chain Profilin | Gly m 3 |
| Fish | Codfish-Parvalbumin | Gad c 1 |
| | Salmon | Sal s 1 |
| Shrimp | Tropomyosin | Pen a 1 |

TABLE 4

Food Allergen Protein Families of Animal
Origin, including the following:

| Allergen Family | Examples of Source and Allergen |
|---|---|
| Tropomyosins | Brown shrimp (Pen a 1), Crab (Cha f 1), Oyster (Cra g 1, Cra g) |
| Parvalbumin | Salmon (Sal s 1.01 ), Tuna (Thu o 1.01 ), Carp (Cyp c 1.01), Frog (Ran e 1) |
| Caseins | Cow (Bas d 8) |

TABLE 5

Food Allergen Protein Families of Plant
Origin, including the following:

| Allergen Family | Examples of Source and Allergen |
|---|---|
| 11 S (legumin like) globulins | Peanut (Ara h3, Ara h4), Soy (Glycinin), Buckwheat (Fag e 1), Cashew (Ana o 2) |
| Bet v 1 superfamily | Apple (Mal d 1), Cherry (Pm av 1 ), Pear (Pyr c 1), Carrot (Dau c 1) |
| Nonspecific lipid transfer proteins | Apricot (Pru ar 3), Cherry (Pm av 3), Peach (Pm p 3), Strawberry (Fra a 3), Grape (Vit v 1), Walnut (Jug r 3), Lettuce (Lac s 1), Corn (Zea m 14) |
| Chitinases | Avocado (Pers a 1), Banana (Mus xp Chitinase) |
| Profilins | Pear (Pyr c 4), Cherry (Pm av 4), Celery (Api g 4), Latex (Hev b 8) |

In some embodiments are provided compositions described herein, suited for oral, subcutaneous or sublingual administration, comprising non-food allergens, sources of which allergens can include, without limitation, the following:

TABLE 6

Grass Pollen Allergens, including components
of the following species:

| Scientific Name | Examples of Component allergens |
|---|---|
| Paspalum notatum | Pas n 1, 13 |
| Cynodon dactylon | Cyn d 1-14 |
| Sorghum ha/epense | Sor h 1-14 |
| Phleum pratense | Phl p 1-14 |
| Lolium perenne | Lol p 1-14 |
| Poa pratensis | Poa p 1-14 |

TABLE 7

Weed Pollen Allergens, including components
of the following species:

| Scientific Name | Examples of Component allergens |
|---|---|
| Ambrosia artemisiifolia | Amb a 1-10 profilin, and cystatin |
| Artemisia vulgaris | Art v 1-3 and profilin |
| Parietaria spp. | Par o 1 and 2 |

TABLE 8

Indoor Allergens, including components of following species
of dust mites, storage mites, animals, and insects:

| Scientific Name | Examples of Component allergens |
|---|---|
| Dermatophagoides farinae | Der f 1, 2, 3, 7, 10, 11, 14, 15-17, 18w |
| Dermatophagoides pteronyssinus | Der p 1-11, 14, 20 |
| Euroglyphus maynei | Eur m 2, 14 |
| Blomia tropicalis | Blo t 1-9, 13, 21 |
| Lepidoglyphus destructor | Lep d 2, 5, 7, 10, 13 |
| Glycyphagus domesticus | Glyd 2 |
| Tyrophagus putrescentia | Tyr p 2, 13 |
| Canis familiaris | Can f 1-4 |
| Felis domesticus | Fel d 1-4, 5w-7w |
| Equus caballus | Equ ca 1-5 |
| Cavia porcellus | Cav p 1, 2 |
| Mus musculus | Mus m 1 |
| Rattus norvegius | Rat n 1 |
| Blattella germanica | Bla g 1-6 |
| Periplaneta americana | Per a 1, 3, 7 |

TABLE 9

Mold Allergens, including components of the following species:

| Scientific Name | Examples of Component allergens |
|---|---|
| Alternaria alternata | Alt a 1-12 |
| Cladosporium herbarum | Cla h 1-12 |
| Aspergillus fumigates | Asp f 1-22 |
| Penicillium chrysogenum | Pen ch 13, 18, 20 |

TABLE 10

Tree Pollen Allergens, including components
of the following species:

| Scientific Name | Examples of Component allergens |
|---|---|
| Fraxinus | Fra a 1 |
| Betulaceae | Bet v 1-7 |
| Juniperus | Jun a 1-3 |
| Quercus | Que a 1 |
| Oleaceae | Ole e 1-8 |
| Platanus | Pia a 1 |

TABLE 11

Stinging Insect Allergens, including components of the following:

| Subfamily Name | Examples of Component allergens |
|---|---|
| Honeybee | Api m 1 (Phospholipase A2) |
| | Api m 2 (Hyaluronidase) |
| | Api m 3 (Acid phosphatase) |
| | Api m 4 (Melittin) |
| Bumblebee | Born p 1 (Phospholipase A2) |
| | Born p 4 (Protease) |
| Vespinae and Polistinae | Grp 1 (Phospholipase A 1) |
| | Grp 2 (Hyaluronidase) |
| | Grp 3 (Acid phosphatase) |
| | Grp 4 (Protease) |
| | Grp 5 (Antigen 5) |
| Fire ants | Sol i 1 (Phospholipase A 1) |
| | Sol i 2 (Unknown protein) |
| | Sol i 3 (Antigen 5 protein family) |
| | Sol i 4 |

As an example, a peanut derivative such as peanut powder, butter or protein can be loaded into a sterically stabilized liposome carrier for administration as part of an allergy treatment. As another example, multiple allergens can be loaded into a single liposome. Optionally, MPL is loaded in the liposome in combination with the allergen. The administration can be subcutaneous, sublingual, or oral.

The methods disclosed herein can comprise administering compositions comprising an allergy medication for instance selected from the group consisting of an antihistamine, a corticosteroid, a bronchodilator, a mast cell stabilizer, a leukotriene inhibitor, an anti-tuberculosis agent, a serine lung protease inhibitor, and any combination and derivative thereof which may optionally be administered concurrently or subsequently with an allergen which may be administered separately or as part of the same composition.

In some cases, the antihistamine comprises a $H_1$-antihistamine, $H_2$-antihistamine, $H_3$-antihistamine, $H_4$-antihistamine, or any combination thereof. In some cases, the $H_1$-antihistamine comprises acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine, pheniramine, phenyltoloxamine, promethazine, quetiapine, rupatadine, tripelennamine, triprolidine, cetirizine, desloratadine, pyrilamine, or any combination or derivative thereof. In some cases, the $H_2$-antihistamine comprises cimetidine, famotidine, lafutidine, nizatidine, ranitidine, roxatidine, tiotidine, or any combination or derivative thereof. In some cases, the $H_3$-antihistamine comprises clobenpropit, ABT-239, ciproxifan, conessine, A-349,821, thioperamide, or any combination or derivative thereof. In some cases, the $H_3$-antihistamine comprises thioperamide, JNJ 7777120, VUF-6002, or any combination or derivative thereof.

In some cases, the corticosteroid comprises budesonide, flunisolide, triamcinolone, beclomethasone, fluticasone, mometasone, dexamethasone, hydrocortisone, methylprednisolone, prednisone, cortisone, betamethasone, or any combination or derivative thereof.

In some cases, the bronchodilator comprises terbutaline, albuterol, ipatropium, pirbuterol, epinephrine, salmeterol, levalbuterol, formoterol, or any combination or derivative thereof.

In some cases, the mast cell stabilizer comprises β2-adrenergic agonists, cromoglicic acid, ketotifen, methylxanthines, olopatadine, omalizumab, pemirolast, quercetin, or any combination or derivative thereof.

In some cases, the leukotriene inhibitor comprises montelukast, zafirlukast, zileuton, or any combination or derivative thereof.

In some cases, the anti-tuberculosis agent comprises isoniazid, ethambutol, pyrazinamide, rifamycin, rifampin, streptomycin, clarithromycin, or any combination or derivative thereof.

In some cases, the at least one agent comprises gangamycin, azelastine, theophylline, amikacin, gentamicin, tobramycin, rifabutin, rifapentine, sparfioxacin, ciprofloxacin, quinolones, azithromycin, erythromycin, or any combination or derivative thereof.

Oral desensitization can be used for treating an allergy or inducing tolerance to an allergen, such as peanut allergy. Oral desensitization can be the administration of measured amounts of an allergen (e.g., peanut powder, butter or protein) to an allergic individual, in an incremental manner till the individual can ingest the allergen without having a reaction. In some cases, a daily, weekly, biweekly, monthly, quarterly, biennial or annual dose of the allergen may continue for years, or even for a lifetime.

Allergy, for instance food allergy, can include a number of conditions caused by hypersensitivity of the immune system to a particular allergen. It can be defined by an elevated Immunoglobulin E (IgE) antibody level to the particular allergen. Tolerance is a process that resets the IgE antibody production, and thereby can allow an individual to tolerate exposure to that allergen without a reaction. In some cases, a certain level of bacterial endotoxin (PAMP-lipid mediators) is needed for antigen presenting cells (e.g., dendritic cells) to present to T lymphocyte regulatory cells (T reg cells) to turn off signals so sensitization does not occur. If the level of lipid mediators is below or inadequate, it can result in a loss of regulation of the immune system, mainly the T lymphocyte regulatory cells (T reg cells). This loss of regulation can allow B lymphocytes producing IgE specific to an allergen, such as peanut, to be unregulated, thereby allowing for sensitization to that allergen. In some cases, the level of bacterial antigens or endotoxin, such as a lipid mediator, may play a role in resetting the T regulatory system. One such example of a lipid mediator is Lipid A, which is a bacterial endotoxin. In some cases, the Lipid A can be Monophosphoryl Lipid A (MPL), which is a Toll-like receptor TLR-4 agonist. TLR-4 can play a role in the innate immune system, for example, with dendritic cells. TLR-4 can also have an impact on the T regulatory system therefore playing a role in resetting the balance of the immune system. These immunomodulating lipids can decrease the pro-inflammatory cytokines such as IL-4 and IL-5 which drive the inflammatory cascade. In addition, these immunomodulating lipids can also increase IL-10 which is a cytokine that supports the innate system and/or drives T-regulatory lymphocytes.

Also disclosed are methods for treating allergic inflammations which are non-airway inflammations by administering orally, sublingually or subcutaneously a pharmaceutical composition described herein. In some cases, the treatment is with allergen desensitization to the food (immunotherapy). In some cases, the methods comprise administering an allergen (e.g., in incremental doses) via injections administered subcutaneously (SCIT), e.g. "allergy shots". In some cases, the methods comprise administering an allergen (e.g., in incremental doses) under the tongue (sublingual immunotherapy—SLIT). In some cases, the methods comprise administering an allergen (e.g., in incremental doses) orally.

Compositions and Methods of Treating an Inflammatory Disorder

The compositions and methods disclosed herein can be used for treating an inflammatory disorder. For example, the inflammatory disorder can be an undesired gut or esophagus inflammatory response (e.g. eosinophilic esophagitis). The pharmaceutical composition is suitable for subcutaneous, sublingual, or oral administration.

The compositions can comprise or be co-administered with one or more agent for treating another condition (e.g. an allergy). For example, the compositions can be administered with one or more food allergen. The sterically stabilized liposome carrier can have an inherent calming property to the gut, and/or can be used for reducing inflammation (e.g. in the gut). One or more agent, such as allergen, corticosteroid, anti-IgE antibody, MPL, or any combination thereof, can be formulated with or co-administered or sequentially administered with a sterically stabilized liposome carrier to treat the inflammatory disorder.

In some cases, the corticosteroid comprises budesonide, flunisolide, triamcinolone, beclomethasone, fluticasone, mometasone, dexamethasone, hydrocortisone, methylprednisolone, prednisone, cortisone, betamethasone, or any combination or derivative thereof.

In some cases, the at least one agent comprises azelastine, theophylline, amikacin, gentamicin, tobramycin, rifabutin, rifapentine, sparfioxacin, ciprofloxacin, quinolones, azithromycin, erythromycin, or any combination or derivative thereof.

A composition described herein, comprising sterically stabilized liposome carrier can be administered orally, sublingually or subcutaneously for treating an inflammatory disorder which is not an airway inflammation. In some cases, the composition can further comprise one or more agent for treating the inflammatory disorder. In some cases, the composition can further comprise one or more agent for treating another condition (e.g., a food allergy).

Methods of Treating Eosinophilic Esophagitis (EoE)

Eosinophilic esophagitis (EoE) is a chronic immune system disease. In EoE, a type of white blood cell (eosinophil) can build up in the lining of the tube that connects mouth to stomach (esophagus). This buildup, which can be a reaction to foods and/or allergens, can inflame or injure the esophageal tissue. Damaged esophageal tissue can lead to difficulty swallowing or cause food to get caught when you swallow.

Disclosed herein are compositions, kits, and methods relating to oral, sublingual or subcutaneous administration of a sterically stabilized liposome carrier for treating EoE. In some cases, the pharmaceutical compositions comprise a therapeutically effective amount of at least one agent for treating EoE. In some cases, the pharmaceutical composition can comprise MPL and/or steroids such as budesonide and triamcinolone. In some cases, immunomodulating lipids can also play a role in decreasing inflammation, and thus be used in treating the inflammatory disorder.

Disclosed herein are methods of administering a pharmaceutical composition comprising a therapeutically effective amount of at least one agent for treating eosinophilic esophagitis. The pharmaceutical composition is suitable for subcutaneous, sublingual, or oral administration. The at least one agent can comprises a proton-pump inhibitor (PPI), a corticosteroid, or any combination or derivative thereof. In some cases, the proton-pump inhibitor comprises omeprazole, lansoprazole, dexlansoprazole, esomeprazole, pantoprazole, rabeprazole, ilaprazole, or any combination or derivative thereof. In some cases, the corticosteroid comprises budesonide, flunisolide, triamcinolone, beclomethasone, fluticasone, mometasone, dexamethasone, hydrocortisone, methylprednisolone, prednisone, cortisone, betamethasone, or any combination or derivative thereof. In some cases, the at least one agent comprises azelastine, theophylline, amikacin, gentamicin, tobramycin, rifabutin, rifapentine, sparfioxacin, ciprofloxacin, quinolones, azithromycin, erythromycin, or any combination or derivative thereof.

The compositions can be co-administered with one or more agent for treating another condition (e.g. an allergy). For example, the compositions can be administered with one or more allergen. The sterically stabilized liposome carrier can have an inherent calming property to the gut, and/or can be used for reducing inflammation (e.g. in the gut). One or more agent, such as allergen, steroid, anti-IgE antibody, MPL, and any combination thereof, can be co-administered with the sterically stabilized liposome carrier to treat eosinophilic esophagitis.

Methods of Treating Tuberculosis

Tuberculosis (TB) is an infectious disease caused by the bacterium *Mycobacterium tuberculosis* (MTB). Tuberculosis can affect the lungs. Tuberculosis can also affect other parts of the body. MPL can play a role in the interaction of macrophages and dendritic cells, both cell types which can have important role in controlling the TB infection by the body. Anti-TB agents can have sustained effect as a once a week therapy.

Disclosed herein are compositions, kits, and methods of using a sterically stabilized liposome carrier for treating TB. In some cases, a pharmaceutical composition comprising a therapeutically effective amount of at least one agent for treating TB can be used. In some cases, the pharmaceutical composition can comprise MPL and/or steroids such as Isoniazid, Gangamycin, and Streptomycin.

Disclosed herein are methods of administering a pharmaceutical composition comprising a therapeutically effective amount of at least one agent for treating TB. The pharmaceutical composition is suitable for subcutaneous, sublingual, or oral administration. The at least one agent can comprises isoniazid, rifampin (rifadin, rimactane), ethambutol (myambutol), pyrazinamide, fluoroquinolone, amikacin, kanamycin, capreomycin, gangamycin, streptomycin, bedaquiline, linezolid, or any combination or derivative thereof. In some cases, the at least one agent comprises isoniazid. In some cases, the at least one agent comprises gangamycin. In some cases, the at least one agent comprises streptomycin. The pharmaceutical composition further comprises MPL.

Kits

A kit according to the invention can include at least one dosage forms, e.g., one or more dosage forms. In some cases, the kit includes sufficient doses for a period of time. In particular cases, the kit includes a sufficient dose of the pharmaceutical composition for a day, a week, 14 days, 28 days, 30 days, 90 days, 180 days, a year, etc. In some specific cases, the each dose is physically separated into a compartment, in which each dose is segregated from the others.

In some cases, the kit can contain one or more pharmaceutical composition, in a form that requires further processing. For example, the one or more pharmaceutical composition can be in powder form (e.g., table and capsule) and the kit can contain a solution that is used to recombine the power with the solution, e.g., 0.9% NaCl solution. In some case, this reconstituted powder solution can be administered at various locations. In some cases, the powder is contained into a container that can be used as an applicator.

In particular cases, the kit may advantageously be a blister pack. Blister packs are known in the art, and generally include a clear side having compartments (blisters or bubbles), which separately hold the various doses, and a backing, such as a paper, foil, paper-foil or other backing, which is easily removed so that each dose may be separately extracted from the blister pack without disturbing the other doses. In some cases, the kit may be a blister pack in which each day's dose of the pharmaceutical composition. In some cases, the kit may be a blister pack in which each week's dose of the pharmaceutical composition. In some cases, the kit may be a blister pack in which each month's dose of the pharmaceutical composition. In some such cases, the blister pack may have perforations, which allow each daily, weekly, or monthly dose to be separated from the others by tearing it away from the rest of the blister pack. The separate dosage forms may be contained within separate blisters. Segregation of the two pharmaceutical compositions into separate blisters can be advantageous in that it prevents separate dosage forms (e.g. tablet and capsule) from contacting and damaging one another during shipping and handling. Additionally, the separate dosage forms can be accessed and/or labeled for administration to the patient at different times.

In other cases, the kit may be box having separate compartments with separate lids. For example, a kit may comprise a box having seven compartments, each for a separate day of the week, and each compartment marked to indicate which day of the week it corresponds to. In some specific cases, each compartment is further subdivided to permit segregation of one pharmaceutical composition from another. As stated above, such segregation is advantageous in that it prevents damage to the dosage forms and permits dosing at different times and labeling to that effect.

In some cases, the kit may contain written instructions, in any language, directing a subject or a physician to use the contents of the kits in a way to effectively treat a condition disclosed herein.

EXAMPLES

Example 1—Materials and Methods

Animals

Six week-old male C57 black 6 mice were purchased from Charles River Laboratories, Inc., Wilmington, MA. The animals were provided with an ovalbumin-free diet and water ad libitum and were housed in an environment-controlled, pathogen-free animal facility. All animal protocols were approved by the Animal Care Committee of the University of Illinois at Chicago, the Medical College of Wisconsin and the Zablocki Veterans Administration Medical Center, and were in agreement with the National Institute of Health's guidelines for the care and use of laboratory animals.

Ovalbumin Sensitization

The animals were sensitized with ovalbumin (OVA). On day 0, each mouse was anesthetized with methoxyflurane given by inhalation. A fragmented heat-coagulated OVA implant was inserted subcutaneously on the dorsal aspect of the cervical region.

For a ten-day period (days 14-24), each mouse was given a 30-minute aerosolization of a 6% OVA solution on alternate days. This method of sensitization led to significant elevations in eosinophil peroxidase (EPO), peripheral blood (PB) eosinophils, and serum IgE levels, along with inflammation as seen on histopathology by day 24.

Each of the doses was given at a volume of 1 milliliter for 2 minutes through use of a chamber. The mouse had skin and whole body exposure and were allowed to breathe freely. All treatment groups were compared with either sensitized untreated (SENS) or unsensitized (Normal) mice.

Drugs and Reagents

BUD for daily therapy was diluted from premixed vials (0.25 mg/ml) commercially available from AstraZeneca Pharmaceutical, Wayne, PA. BUD for encapsulation and N-2-hydroxethylpiperzine-N'-2-ethanesulfonic acid (HEPES) was purchased from Sigma Chemical, St. Louis, MO. Phosphatidylcholine (PC), phosphatidylglycerol (PG), and poly (ethylene glycol)-distearoylphosphatidylethanolamine (PEG-DSPE) were obtained from Avanti Polar Lipids, Alabaster, AL. Cholesterol was purchased from Calbiochem, La Jolla, CA. NaCl and KCl were purchased from Fisher Scientific, Pittsburgh, PA.

Liposome Preparation

Budesonide (BUD) was encapsulated into either sterically stabilized (phosphatidylglycerol-phosphotidylcholine-poly (ethylene glycol)-cholesterol:distearoylphosphatidylethanolamine):(phosphatidyl glycerol [PG]:phosphatidylcholine [PC]:cholesterol:poly(ethylene glycerol) [PEG] distearoylphosphatidylethanolamine [DSPE]—[PG:PC:Cholesterol:PEG-DSPE] (2:8:5:0.5) sterically stabilized liposomes or conventional (phosphatidylglycerol-phosphatidylcholine-cholesterol) (2:8:5) as a carrier through use of a modified protocol derived from the protocol described by Gangadharam, et al., Antimicrob Agents Chemother, 1995:39:725-730.

Triamcinolone (TRI) was encapsulated into either sterically stabilized (phosphatidylglycerol-phosphatidylcholine-poly (ethylene glycol)-cholesterol:distearoylphosphatidylethanolamine):(phosphatidyl glycerol [PG]: phosphatidylcholine [PC]:cholesterol:poly(ethylene glycerol) [PEG] distearoylphosphatidylethanolamine [DSPE]—[PG:PC:Cholesterol:PEG-DSPE] (2:8:5:0.5) sterically stabilized liposomes.

A portion of the cholesterol used in control liposomes was replaced by BUD or TRI dissolved in chloroform-methanol (2:1) during the preparation of the lipid mixture. The resulting composition was PG:PC:Cholesterol:PEG-DSPE:BUD (2:8:3:0.5:2). Lipids were dried onto the sides of a round-bottomed glass flask or glass tube by rotary evaporation. The dried film was then hydrated by adding sterile 140 mmol/L, NaCl and 10 mmol/L HEPES (pH 7.4) and vortexing.

The resulting multilamellar liposome preparations were extruded 21 times through polycarbonate membranes (either 0.2 or 0.8 μm in pore diameter), (Nuclepore, Pleasanton, CA) through use of an Avestin extrusion apparatus, Toronto, Canada. The control carriers were prepared the same way and of the same composition except that no BUD was added. The resulting multilamellar liposome preparation contained about 96.8 weight percent water and was diluted to suitable concentration (20 μg/ml) for administration.

Liposomes without cholesterol were prepared in a similar manner, except that the molar ratio of the lipids were PG:PC:PEG-DSPE (2:8:0.5).

Liposomes containing MPL were prepared in a similar manner, except that the molar ratio of the lipids were PG:PC:MPL:PEG-DSPE (2:8:0.1:0.5). Liposomes containing both MPL and budesonide were also prepared, in the ratio PG:PC:BUD:MPL:PEG-DSPE (2:8:2:0.1:0.5). Both liposomes were extruded 21 times through polycarbonate membranes with a pore diameter of 0.8 μm.

The amounts of lipid used for the Wk-Empty-S group were based on the amount of lipid nebulized for each of the BUD-encapsulated liposomes (1.39 μmol for the sterically stabilized liposomes and 3.19 μmol for the conventional liposomes).

The dose of BUD chosen was based on preliminary dose-response studies with 5 to 50 μg of BUD as follows. Each day, 5, 10, 15, 20 or 50 μg of BUD was administered to groups of sensitized mice, and the dose-dependent effects on the inflammatory parameters were evaluated. These data were compared with data for either a group of sensitized untreated mice (SENS group) or a group of unsensitized mice (Normal group). A 20 μg/ml dose of BUD was shown on histopathologic examination to effectively decrease, PB eosinophils and inflammation of tissues, along with other inflammatory parameters, without evidence of toxicity to the spleen, liver, bone morrow or gastrointestinal tract. In addition, there were no granulomas or abnormalities in any of the tissues evaluated.

Histopathology Observations

Histopathological examinations performed were as follows:

The tissues were removed and fixed with 10% phosphate buffered formalin. Tissue samples were taken from the skin, spleen, liver, gastrointestinal tract, and kidney. The tissues were embedded in paraffin, sectioned at 5 µm thickness and stained with hematoxylin and eosin and analyzed using light microscopy.

Coded slides were examined by a pathologist in a blinded fashion for evidence of inflammatory changes, including epithelial hyperplasia and perivascular edema and accumulation of eosinophils, neutrophils, and mononuclear inflammatory cells. Each of the parameters evaluated was given an individual number score. Objective measurements of histopathological changes include aggregation of eosinophils around blood vessels (perivascular), accumulation of other inflammatory cells, presence of desquamation and hyperplasia of the epithelium, and infiltration of inflammatory cells.

The percentages of eosinophils were obtained by counting the number of eosinophils in 100 white blood cells under a high-power field scope (×100) from the PB smears stained with Wright-Giemsa stain.

Total Serum IgE

Ninety-six well flat bottom plates (Fisher Scientific) were coated with 100 µL per well of 2 µg/ml rat antimouse IgE monoclonal antibody (BD, PharMingen, San Diego, CA), and incubated overnight at 4° C. Serum was added at a dilution of 1:50 and incubated overnight at 4° C. Purified mouse IgE (k isotype, small b allo-type anti-TNP:BD PharMingen) was used as the standard for total IgE. The samples were incubated for one hour with biotin-conjugated rate antimouse IgE (detection antibody purchased from Southern Biotechnology, Birmingham, AL).

Study Groups

Therapy was initiated on day 25, the day after the OVA sensitization was completed. Sensitized animals received treatments for four weeks. Each study group consisted of 20 mice and was followed for a four-week period. Five animals from each treatment group and from each of the two control groups, sensitized and unsensitized, were euthanized by means of an overdose of methoxyflurane inhaled 24 hours after the first treatments were given and then at weekly intervals for four weeks. At each time point, measurements of PB eosinophils, and total serum IgE levels were obtained and histopathologic examination of the tissues was performed.

Data Analysis

Serum Total IgE levels and peripheral blood eosinophil count analyses were performed using the Student t test. Over the Study period, there were no significant increases or decreases in inflammation within each group according to weekly measurements for all of the inflammatory parameters being evaluated. Therefore all the weekly measurements are presented as Cumulative data. A $p<0.05$ was considered to be statistically significant for all of the above statistical comparisons.

Example 2—BUD 1: Comparison of BUD in the Carrier With Conventional Liposomes

| BUD 1: TREATMENT GROUPS | |
|---|---|
| NORMAL | Unsensitized, Untreated Normal mice |
| SENS | Sensitized, Untreated mice |
| Daily BUD | 20 µg of budesonide without Carrier given daily-Standard therapy |
| WK-S-BUD | 20 µg of budesonide in the Carrier given once a week |
| WK-C-BUD | 20 µg of budesonide encapsulated in Conventional Carrier given once a week |
| WK-ES | Buffer loaded empty Carrier without drug given once a week |
| WK-BUD | 20 µg of budesonide without Carrier given once a week |

Figure 2:
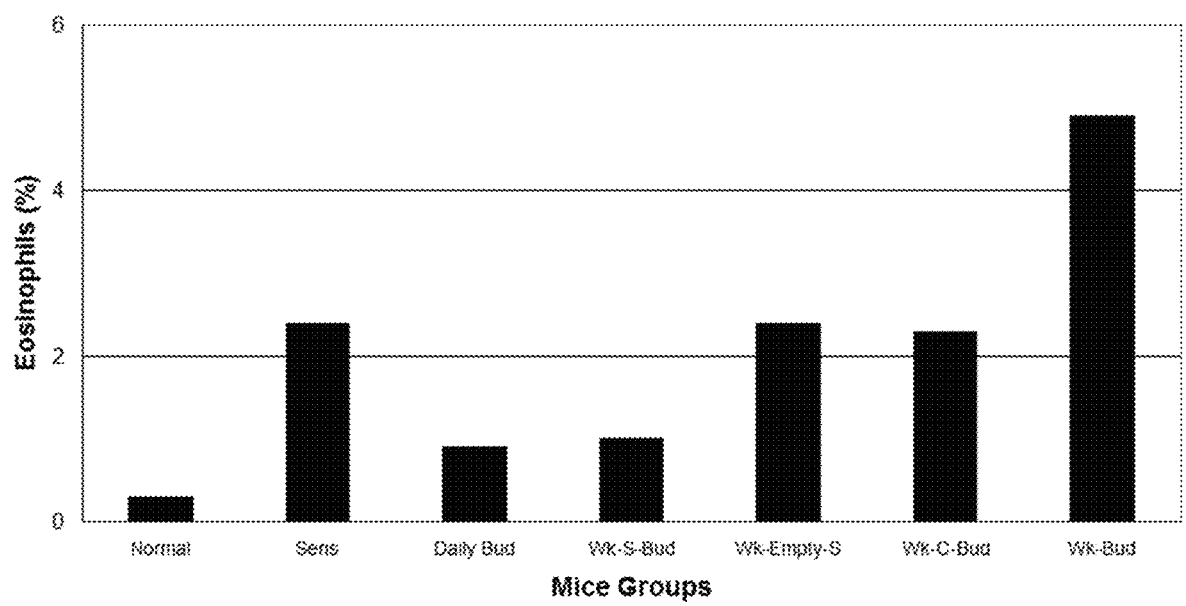
FIG. 2 shows a comparison of PB eosinophil levels in mice, among: NORMAL group (Unsensitized, Untreated Normal mice), Sens group (Sensitized, Untreated mice), Daily Bud group (daily oral administration of 20 µg of budesonide without a sterically stabilized liposome carrier), Wk-S-Bud group (20 µg of a composition described herein, budesonide in a sterically stabilized liposome carrier administered orally once a week), Wk-Empty-S group (Buffer loaded empty sterically stabilized liposome carrier without drug given once a week), Wk-C-Bud group (20 µg of budesonide encapsulated in Conventional Carrier administered once a week), and Wk-Bud group (20 µg of budesonide without a carrier described herein administered once a week).
Figure 3:
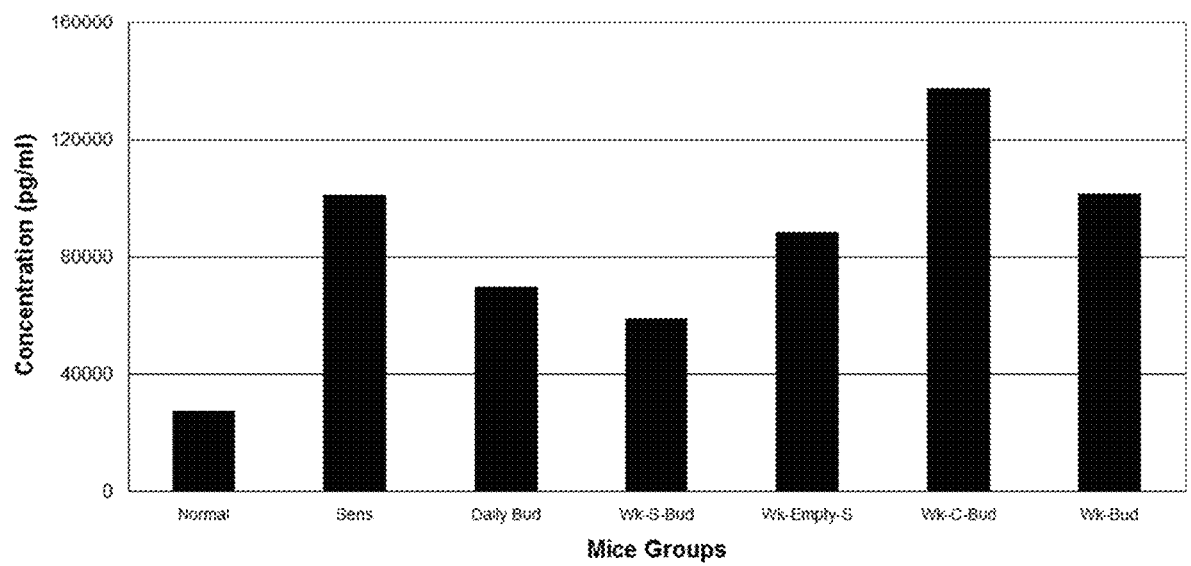
FIG. 3 shows a comparison of IgE levels in mice among: NORMAL group (Unsensitized, Untreated Normal mice), Sens group (Sensitized, Untreated mice), Daily Bud group (20 µg of budesonide without carrier administered orally daily-Standard therapy), Wk-S-Bud group (20 µg of budesonide in a sterically stabilized liposome carrier described herein, administered orally once a week), Wk-Empty-S group (Buffer loaded empty sterically stabilized liposome carrier described herein, administered orally once a week), Wk-C-Bud group (20 µg of budesonide encapsulated in Conventional Carrier given once a week), and Wk-Bud group (20 µg of budesonide without any carrier given once a week).

| BUD 1: RESULTS | | |
|---|---|---|
| | PB Eos (FIG. 2) | IgE levels (FIG. 3) |
| NORMAL | — | — |
| SENS | ↑ | ↑ |
| Daily BUD | ↓ | ↓ |
| WK-S-BUD | ↓ | ↓ |
| WK-C-BUD | ∅ | ∅ |
| WK-ES | ∅ | ∅ |
| WK-BUD | ∅ | ∅ |
| Legend | ↑ | ∅ | ↓ | — |
| | Moderate-Severe inflammation | No significant reduction in inflammation | Significant reduction in inflammation | No inflammation |

In the set of data given for BUD 1, it was demonstrated that one dose of budesonide (BUD) encapsulated in the carrier given once a week (WK-S-BUD), reduced inflammation as effectively as the same dosage of BUD given once a day (Daily BUD) when compared to the Sensitized Untreated group (SENS) and was comparable to the NORMAL group. Weekly treatments with free BUD without Carrier (WK-BUD), BUD encapsulated in Conventional Carrier (WK-C-BUD) and Empty Carrier (WK-ES) did not have comparable effects.

Example 3—BUD 2: Comparison of BUD in the Carrier with Free Drug/Free Carrier Administered Simultaneously

| BUD 2: TREATMENT GROUPS | |
|---|---|
| NORMAL | Unsensitized, Untreated Normal mice |
| SENS | Sensitized, Untreated mice |
| Daily BUD | 20 µg of budesonide without the Carrier given daily-Standard therapy |
| WK-S-BUD | 20 µg of budesonide in the Carrier given once a week |
| WK-ES | Buffer loaded Empty Carrier without drug given once a week |
| WK-BUD | 20 µg of budesonide without the Carrier given once a week |
| WK-BUD & ES | WK-ES and WK-BUD without encapsulation in the Carrier, given once a week |

Figure 4:
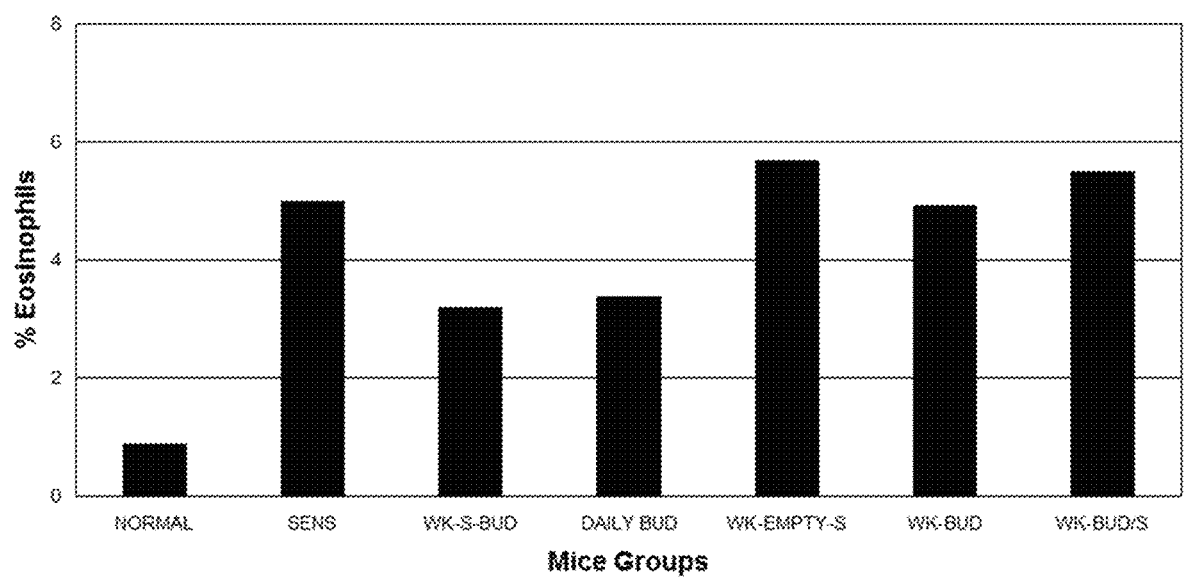
FIG. 4 shows a comparison of PB eosinophil levels among: NORMAL group (Unsensitized, Untreated Normal mice), Sens group (sensitized, Untreated mice), Daily Bud group (20 µg of budesonide without a carrier given daily-Standard therapy), Wk-S-Bud group (20 µg of budesonide in sterically stabilized liposome carrier described herein given orally once a week), Wk-Empty-S group (Buffer loaded empty sterically stabilized liposome carrier described herein without drug given orally once a week), Wk-Bud group (20 µg of budesonide without carrier given orally once a week), and Wk-Bud & ES group (Wk-Empty-S and Wk-Bud without encapsulation in a carrier, given orally once a week).
Figure 5:
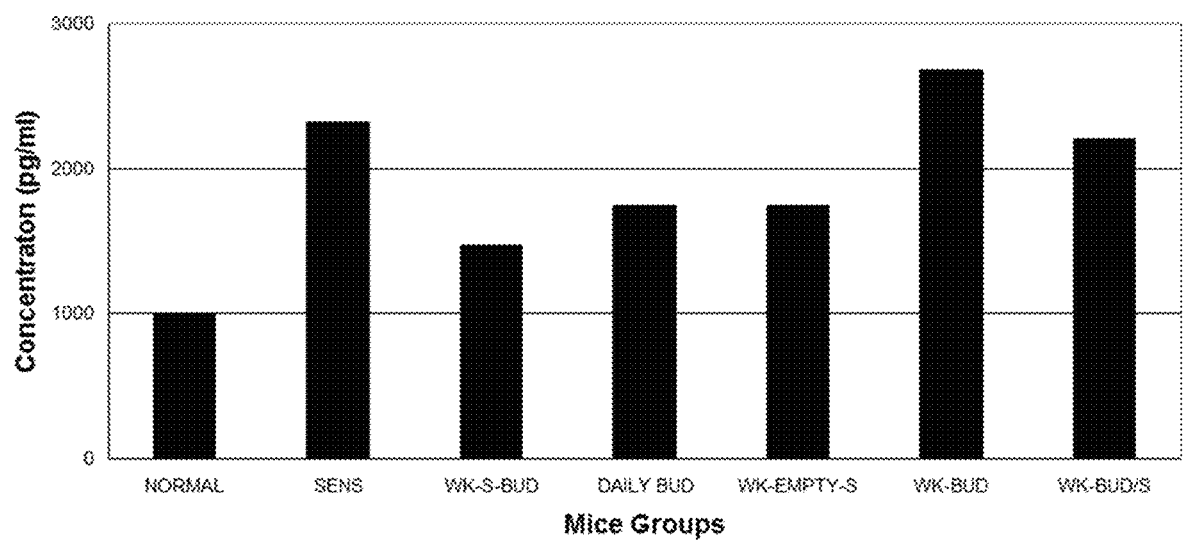
FIG. 5 shows a comparison of IgE levels in mice among: NORMAL group (Unsensitized, Untreated Normal mice), Sens group (Sensitized, Untreated mice), Daily Bud group (20 µg of budesonide without Carrier given daily-Standard therapy), Wk-S-Bud group (20 µg of budesonide in sterically stabilized liposome carrier given orally once a week), Wk-Empty-S group (Buffer loaded empty sterically stabilized liposome carrier without drug given orally once a week), Wk-Bud group (20 µg of budesonide without any carrier given once a week), and Wk-Bud & ES group (Wk-Empty-S and Wk-Bud without encapsulation in the carrier, given once a week).

| BUD 2: RESULTS | | |
|---|---|---|
| | PB Eos (FIG. 4) | IgE levels (FIG. 5) |
| NORMAL | — | — |
| SENS | ↑ | ↑ |
| Daily BUD | ↓ | ↓ |
| WK-S-BUD | ↓ | ↓ |
| WK-ES | ∅ | ∅ |
| WK-BUD | ∅ | ∅ |
| WK-BUD & ES | ∅ | ∅ |

In the set of data given for BUD 2, it was demonstrated that one dose of budesonide (BUD) encapsulated in the Carrier given once a week (WK-S-BUD), reduced inflammation as effectively as the same dosage of BUD given once a day (Daily BUD) when compared to the Sensitized Untreated group (SENS) and was comparable to the NORMAL group. Weekly treatments with only free BUD without Carrier (WK-BUD), Empty Carrier (WK-ES), or free BUD (WK-BUD) and Empty Carrier (WK-ES) given simultaneously did not have comparable effects.

Example 4—BUD 3: Comparison of BUD Encapsulated in the Carrier With and Without Cholesterol

| BUD 3: TREATMENT GROUPS | |
|---|---|
| NORMAL | Unsensitized, Untreated Normal mice |
| SENS | Sensitized, Untreated mice |
| Daily BUD | 20 µg of budesonide without the Carrier given daily-Standard therapy |
| WK-S-BUD + (plus Chol) | 20 µg of budesonide in the Carrier With Cholesterol given once a week |
| WK-S-BUD − (minus Chol) | 20 µg of budesonide in the Carrier Without Cholesterol given once a week |
| WK-ES− | Buffer loaded empty Carrier without cholesterol or drug given once a week |
| WK-BUD | 20 µg of budesonide without the Carrier given once a week |

Figure 6:
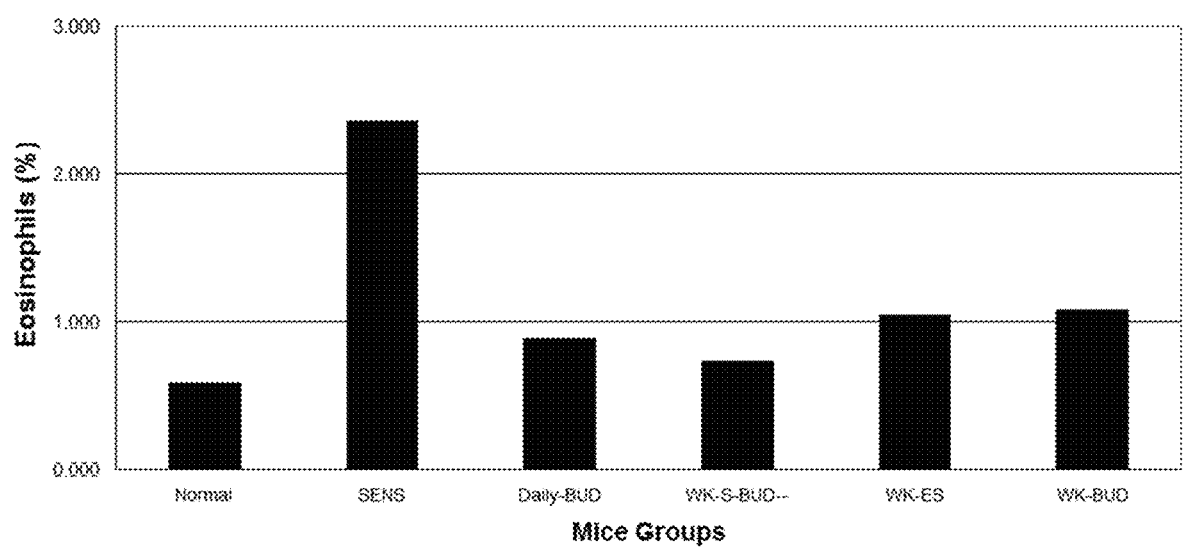
FIG. 6 shows a comparison of PB eosinophil levels among: NORMAL group (Unsensitized, Untreated Normal mice), Sens group (Sensitized, Untreated mice), Daily Bud group (20 µg of budesonide without a carrier given daily-Standard therapy), Wk-S-Bud+group (20 µg of budesonide in the sterically stabilized liposome carrier with cholesterol given orally once a week), Wk-S-Bud–group (20 µg of budesonide in the sterically stabilized liposome carrier without cholesterol given orally once a week), Wk-Empty-S group (Buffer loaded empty carrier without drug or cholesterol given once a week), and Wk-Bud group (20 µg of budesonide without Carrier given once a week).
Figure 7:
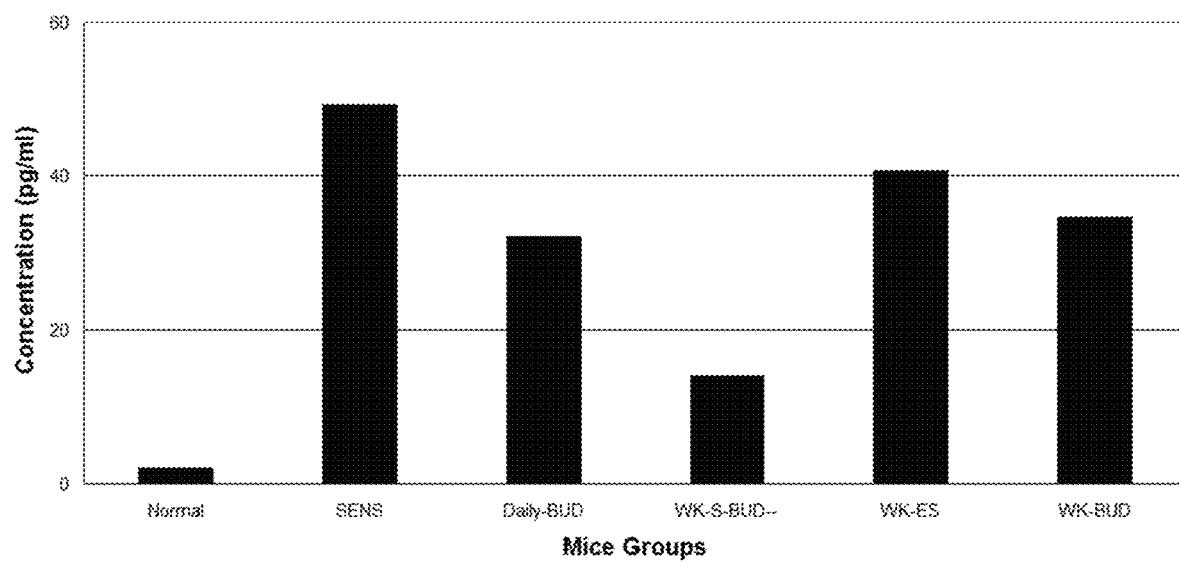
FIG. 7 shows a comparison of IgE levels among: NORMAL group (Unsensitized, Untreated Normal mice), Sens group (Sensitized, Untreated mice), Daily Bud group (20 µg of budesonide without Carrier given daily-Standard therapy), Wk-S-Bud+group (20 µg of budesonide in the sterically stabilized liposome carrier with Cholesterol given orally once a week), Wk-S-Bud--group (20 µg of budesonide in the sterically stabilized liposome carrier without Cholesterol given orally once a week), Wk-Empty-S group (Buffer loaded empty sterically stabilized liposome carrier without drug or cholesterol given once a week), and Wk-Bud group (20 µg of budesonide without carrier given once a week).

| BUD 3: RESULTS | | |
|---|---|---|
| | PB Eos (FIGS. 2, 4 & 6) | IgE levels (FIGS. 3, 5 & 7) |
| NORMAL | — | — |
| SENS | ↑ | ↑ |
| Daily BUD | ↓ | ↓ |
| WK-S-BUD + | ↓ | ↓ |
| WK-S-BUD − | ↓ | ↓ |
| WK-ES − | ∅ | ∅ |
| WK-BUD | ∅ | ∅ |

In the set of data given for BUD 3, it was demonstrated that BUD encapsulated in the Carrier with (WK-S-BUD+) or without Cholesterol (WK-S-BUD−−) given once a week, reduced inflammation as effectively as the same dosage of BUD given once a day (Daily BUD), when compared to the Sensitized Untreated group (SENS) and, was comparable to the NORMAL group. Only the WK-S-BUD+ and WK-S-BUD−− treated groups significantly reduced the BUD in the Carrier without Cholesterol (WK-S-Bud−−) was equally effective as BUD encapsulated in the Carrier with Cholesterol (WK-S-BUD+). Weekly treatments with only free BUD without Carrier (WK-BUD) and Empty Carrier without cholesterol (WK-ES−−) did not have comparable effects on inflammation as the WK-S-BUD+ and WK-S-BUD−− treated groups.

Example 5—BUD 4: Comparison of BUD in the Carrier With and Without MPL

| BUD 4: TREATMENT GROUPS | |
|---|---|
| NORMAL | Unsensitized, Untreated Normal mice |
| SENS | Sensitized, Untreated mice |
| Daily BUD | 20 µg of budesonide without the Carrier given daily-Standard therapy |
| WK-S-BUD − (minus MPL) | 20 µg of budesonide in the Carrier Without MPL given once a week |
| WK-S-BUD + (plus MPL) | 20 µg of budesonide in the Carrier With MPL given once a week |
| WK-ES − | Buffer loaded empty Carrier without drug or MPL given once a week |
| WK-ES-MPL | Buffer loaded empty Carrier without drug, With MPL given once a week |

Figure 8:
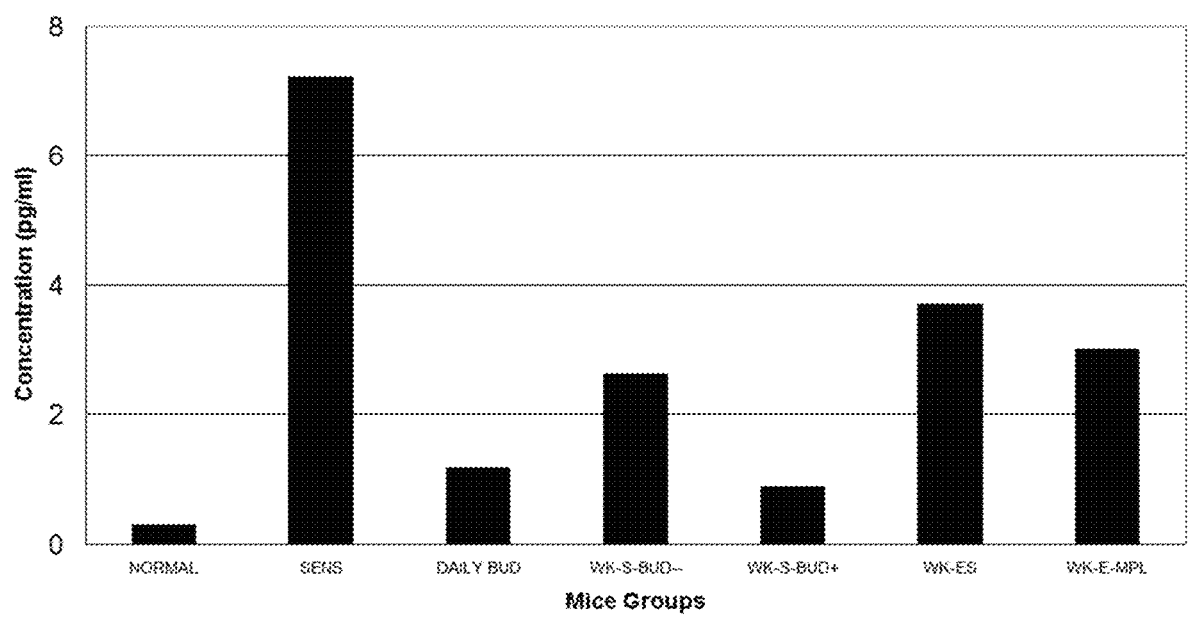
FIG. 8 shows a comparison of IgE levels among: NORMAL group (Unsensitized, Untreated Normal mice), Sens group (Sensitized, Untreated mice), Daily Bud group (20 µg of budesonide without carrier given daily-Standard therapy), Wk-S-Bud+group (20 µg of budesonide in the sterically stabilized liposome carrier with Monophosphoryl lipid A (MPL), given once a week), Wk-S-Bud-group (20 µg of budesonide in the sterically stabilized liposome carrier without MPL given once a week), Wk-Empty-S group (Buffer loaded empty sterically stabilized liposome carrier without drug or MPL given orally once a week), and Wk-Bud group (20 µg of budesonide without a carrier given once a week).

| BUD 4: RESULTS | |
|---|---|
| | IgE levels (FIG. 8) |
| NORMAL | — |
| SENS | ↑ |
| Daily BUD | ↓ |
| WK-S-BUD + | ↓ |
| WK-S-BUD − | ↓ |
| WK-ES − | ∅ |
| WK-ES-MPL | ∅ |

In the set of data given for BUD 4, it was demonstrated that BUD encapsulated in the Carrier with (WK-S-BUD+) or without MPL (WK-S-BUD−−) given once a week, reduced inflammation as effectively as the same dosage of BUD given once a day (Daily BUD) when compared to the Sensitized Untreated group (SENS) and was comparable to the NORMAL group. Only the WK-S-BUD+, WK-S-BUD−−, and the weekly Empty Carrier with MPL (WK-ES-MPL) treatment groups significantly reduced the inflammation. BUD in the Carrier with MPL (WK-S-Bud+) was equally as effective as BUD encapsulated in the Carrier without MPL (WK-S-BUD−−). Weekly treatments with Empty Carrier without MPL (WK-ES−−) did not have comparable effects as the WK-S-BUD+, WK-S-BUD−−, or Empty Carrier with MPL (WK-ES-MPL) treated groups.

Example 6—BUD 5: Comparison of BUD With TRI in the Carrier

| BUD 5: TREATMENT GROUPS | |
|---|---|
| NORMAL | Unsensitized, Untreated Normal mice |
| SENS | Sensitized, Untreated mice |
| Daily BUD | 20 µg of budesonide without the Carrier given daily-Standard therapy |
| WK-S-BUD | 20 µg of budesonide in the Carrier given once a week |
| WK-S-TRI-20 µg | 20 µg of triamcinolone in the Carrier given once a week |

| BUD 5: TREATMENT GROUPS | |
|---|---|
| WK-S-TRI-40 µg | 40 µg of triamcinolone in the Carrier given once a week |
| WK-ES | Buffer loaded empty Carrier without drug given once a week |

Figure 9:
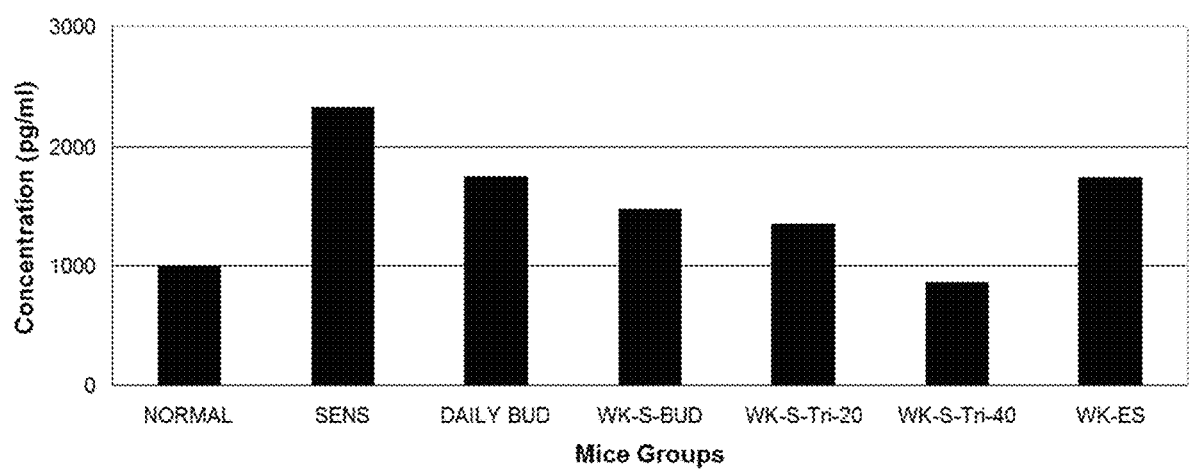
FIG. 9 shows a comparison of IgE levels among: NORMAL group (Unsensitized, Untreated Normal mice), Sens group (Sensitized, Untreated mice), Daily Bud group (20 µg of budesonide without carrier given daily-Standard therapy), Wk-S-Bud group (20 µg of budesonide in the sterically stabilized liposome carrier given once a week), Wk-S-Tri-20 µg group (20 µg of triamcinolone in the sterically stabilized liposome carrier given orally once a week), Wk-S-Tri-40 µg group (40 µg of triamcinolone in the sterically stabilized liposome carrier given orally once a week), and Wk-Empty-S group (Buffer loaded empty sterically stabilized liposome carrier without drug or MPL given orally once a week).

| BUD 5: RESULTS | |
|---|---|
| | IgE levels (FIG. 9) |
| NORMAL | — |
| SENS | ↑ |
| Daily BUD | ↓ |
| WK-S-BUD | ↓ |
| WK-S-TRI-20 µg | ↓ |
| WK-S-TRI-40 µg | ↓ |
| WK-ES | ∅ |

In the set of data given for BUD 5, it was demonstrated that 20 µg of Triamcinolone (TRI) encapsulated in the Carrier (WK-S-TRI-20 µg) or 40 µg of TRI encapsulated in the Carrier (WK-S-TRI-40 µg) given once a week, reduced inflammation as effectively as 20 µg of Budesonide (BUD) encapsulated in the Carrier with (WK-S-BUD) or BUD given once a day (Daily BUD) when compared to the Sensitized Untreated group (SENS) and was comparable to the NORMAL group. WK-S-TRI-20 µg, WK-S-TRI-40 µg, WK-S-BUD, and Daily BUD all reduced the inflammation.

Example 7—Pro-Inflammatory Cytokines Levels

| TREATMENT GROUPS | |
|---|---|
| NORMAL | Unsensitized, Untreated Normal mice |
| SENS | Sensitized, Untreated mice |
| D-Bud | 20 µg of budesonide without the Carrier given daily-Standard therapy |
| WK-BUD | 20 µg of budesonide in the Carrier given once a week |
| WK-ES | Buffer loaded empty Carrier without drug given once a week |

Results

Figure 10:
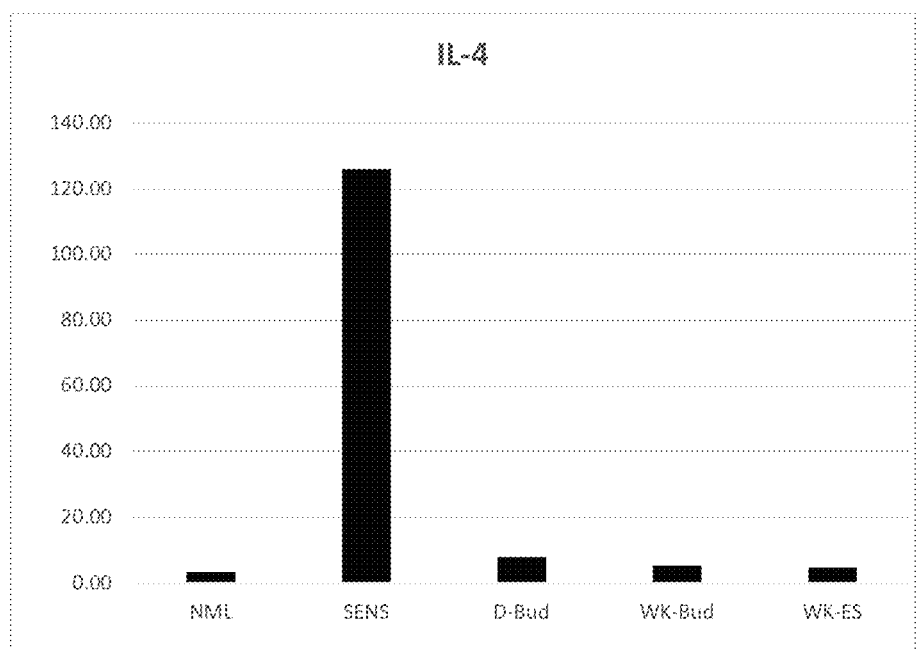
FIG. 10 shows that once a week administration of the empty sterically stabilized drug delivery system (WK-ES) and once a week oral administration of Budesonide encapsulated in the sterically stabilized liposome carrier significantly decreased levels of the pro-inflammatory cytokine IL-4.
Figure 11:
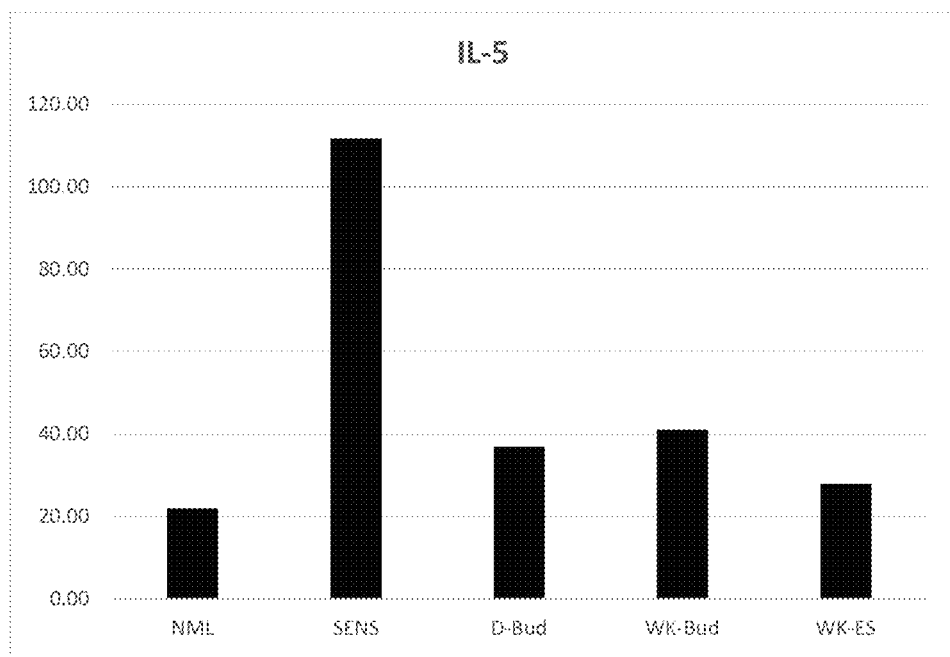
FIG. 11 shows that once a week oral administration of the empty sterically stabilized drug delivery system (WK-ES) and once a week oral administration of Budesonide encapsulated in the sterically stabilized liposome carrier significantly decreased levels of the pro-inflammatory cytokine IL-5.

As shown in FIGS. 10 and 11, once a week administration of the empty sterically stabilized drug delivery system (WK-ES) and once a week administration of Budesonide encapsulated in the sterically stabilized drug delivery system significantly decreased levels of the pro-inflammatory cytokines IL-4 and IL-5.

Example 8—Anti-Inflammatory Cytokines Levels

| TREATMENT GROUPS | |
|---|---|
| NORMAL | Unsensitized, Untreated Normal mice |
| SENS | Sensitized, Untreated mice |
| D-Bud | 20 µg of budesonide without the Carrier given daily-Standard therapy |
| WK-BUD | 20 µg of budesonide in the Carrier given once a week |
| WK-ES | Buffer loaded empty Carrier without drug given once a week |

Results

Figure 12:
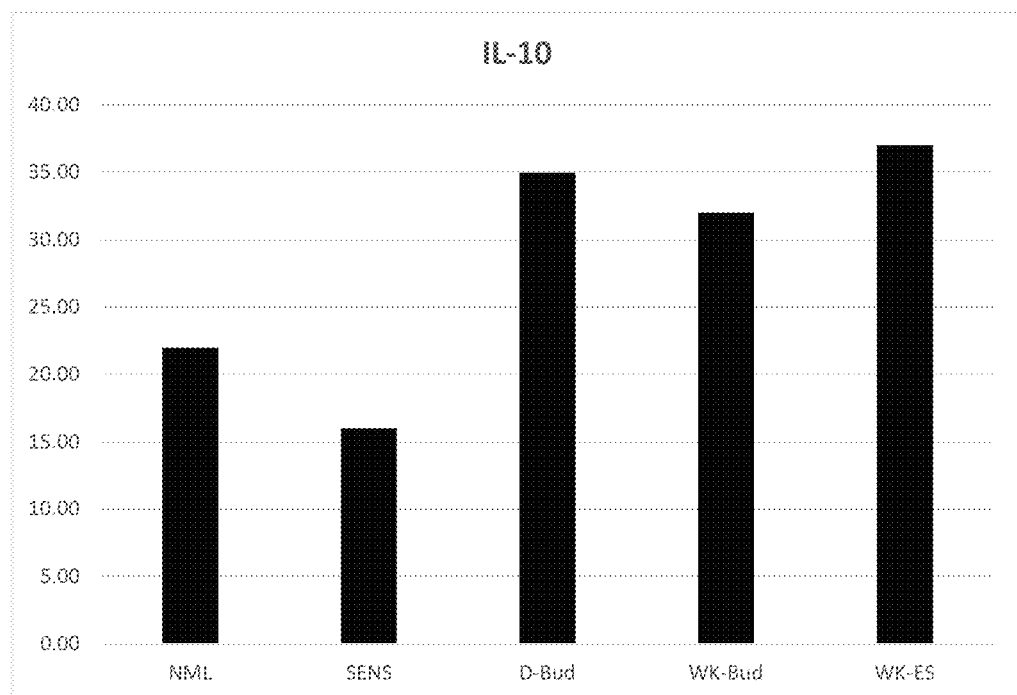
FIG. 12 shows that once a week oral administration of the empty sterically stabilized drug delivery system/carrier (WK-ES) and once a week oral administration of Budesonide encapsulated in the sterically stabilized liposome carrier significantly increased levels of the anti-inflammatory cytokine IL-10.

As shown in FIG. 12, once a week administration of the Empty sterically stabilized drug delivery system (WK-ES) and once a week administration of Budesonide encapsulated in the sterically stabilized drug delivery system significantly increased levels of the anti-inflammatory cytokine IL-10.

Example 9—Stained Slides of Skin

Figure 13:
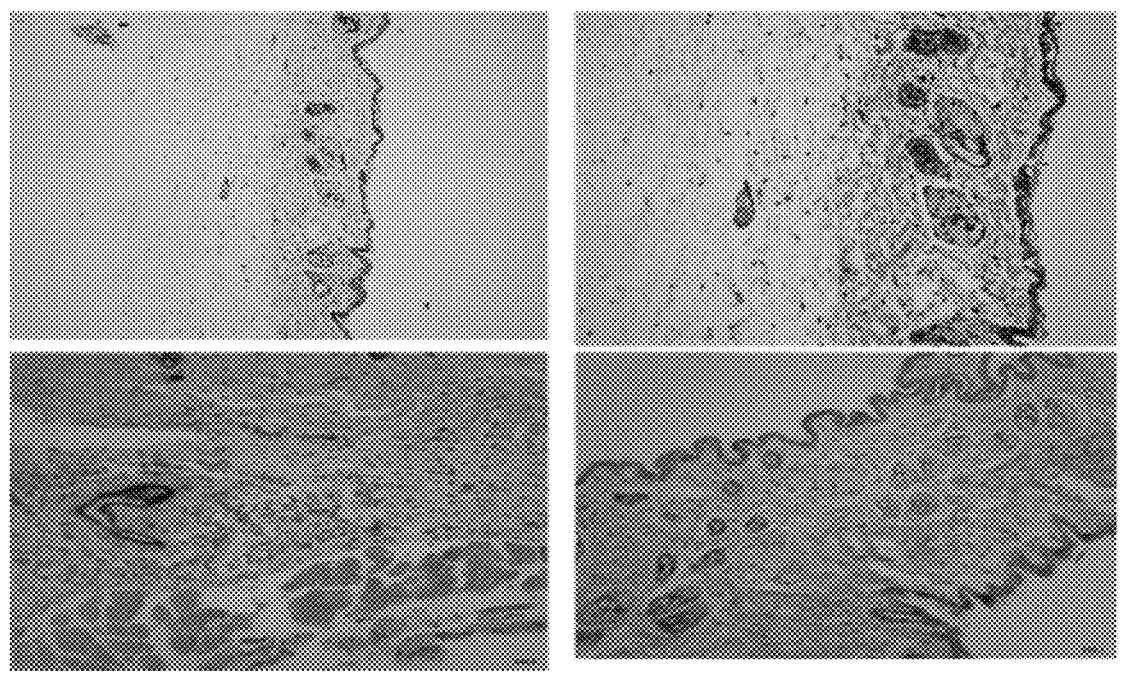
FIG. 13 shows hematoxylin and eosin stained slides of skin. Top two frames show Empty sterically stabilized liposome carrier administered orally once a week to a sensitized mouse with allergic inflammation (10× magnification-top left and 40× magnification-top right). Bottom two frames show untreated sensitized mice at 40× magnification.

FIG. 13 illustrated hematoxylin and eosin stained slides of skin. Top two frames show Empty delivery system administered once a week to a sensitized mouse with allergic inflammation (10× magnification-top left and 40× magnification-top right). Bottom two frames show untreated sensitized mice at 40× magnification. There was a significant decrease in inflammation in the treated group when compared to the untreated, sensitized group.

Example 10—Stained Slides of Gastrointestinal Tract

Figure 14:
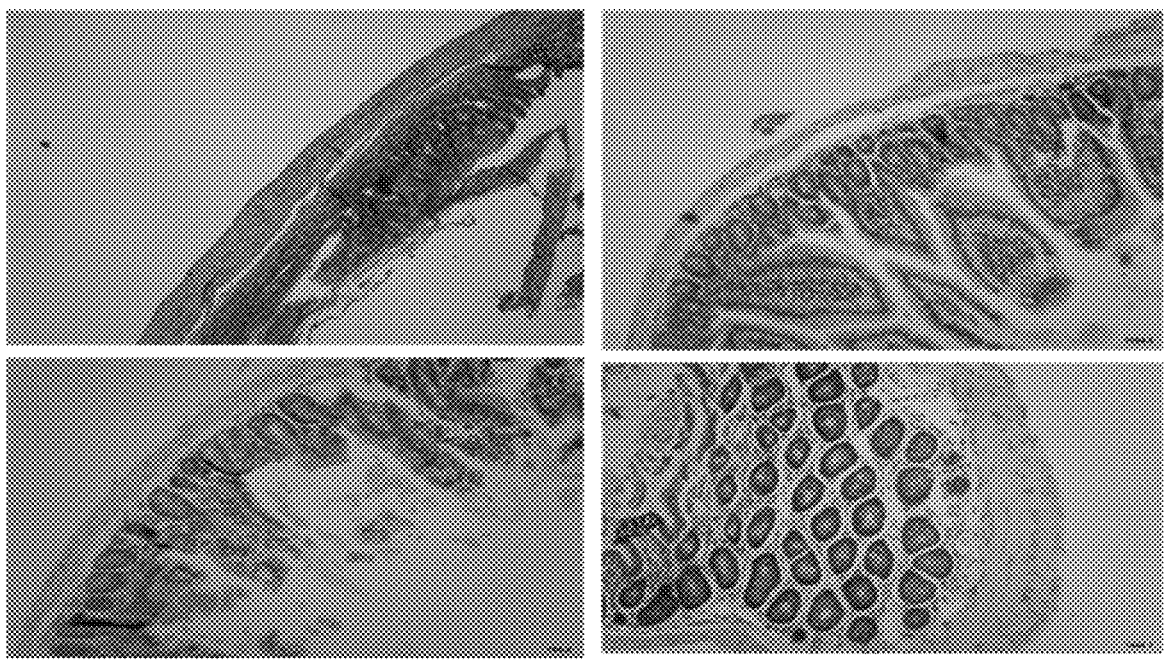
FIG. 14 shows hematoxylin and eosin stained slides of gastrointestinal tract. Top left is empty sterically stabilized liposome carrier delivered orally once a week to a sensitized mouse with allergic inflammation. Top right depicts once a week budesonide encapsulated in the sterically stabilized liposome carrier given orally once a week to a sensitized mouse with allergic inflammation. Bottom left is an example of a Normal untreated mouse. Right bottom is an example of inflammation in an untreated, sensitized mouse with allergic inflammation.

FIG. 14 illustrated hematoxylin and eosin stained slides of gastrointestinal tract. Top left is empty delivery system delivered once a week to a sensitized mouse with allergic inflammation. Top right depicts once a week budesonide encapsulated in the delivery system given once a week to a sensitized mouse with allergic inflammation. Bottom left is an example of a Normal untreated mouse. Right bottom is an example of inflammation in an untreated, sensitized mouse with allergic inflammation. There was a significant decrease in inflammation in the treated groups when compared to the untreated and normal groups.

Example 11—Oral Application of Budesonide for Treating EoE

The safety and efficacy of the oral steroid for EoE will be accessed with four groups for a period of 6 weeks. Each group will consist of 10 patients per group. Group 1 will be the untreated group. Group 2 will be treated with conventional treatment. Group 3 will be administered 100 or 200 micrograms of budesonide encapsulated in the delivery system daily via oral administration. Group 4 will be administered 100 or 200 micrograms of budesonide encapsulated in the delivery system once a week via oral administration.

The liposome preparation will be similar to the procedures used in Example 1. Specifically, the conventional treatment will using 100 or 200 micrograms of budesonide encapsulated in a conventional carrier of phosphatidylglycerol:phosphatidylcholine:cholesterol at 2:8:5. In one example, the delivery systems used in Groups 3 and 4 will be PG:PC:Cholesterol:PEG-DSPE at 2:8:5:0.5. In another example, the delivery systems will be PG:PC:PEG-DSPE at 2:8:0.5.

Example 12—Oral Application of Peanut Allergen

The safety and efficacy of oral application of peanut allergen will be accessed with two sets of experiments, each with four groups, as shown below.

| | Group 1 | Group 2 | Group 3 | Group 4 |
|---|---|---|---|---|
| Set 1 | Untreated group | Conventional Treatment | pH sensitive delivery system | pH sensitive delivery system |

| | Group 1 | Group 2 | Group 3 | Group 4 |
|---|---|---|---|---|
| Set 2 | Untreated group | Conventional Treatment | given with encapsulated peanut peptides pH resistant delivery system given with encapsulated peanut peptides | given with peanut powder pH resistant delivery system given with peanut powder |

The liposome preparation will be similar to the procedures used in Example 1. Specifically, the conventional treatment will use peanut peptides encapsulated in a conventional carrier of phosphatidylglycerol:phosphatidylcholine:cholesterol at 2:8:5. In one example, the delivery systems will use PG:PC:Cholesterol:PEG-DSPE at 2:8:5:0.5. In another example, the delivery systems will be PG:PC:PEG-DSPE at 2:8:0.5. The pH sensitive delivery system will have an additional pH sensitive component, e.g. N-palmitoyl homocysteine (PHC), with the same molar amount as PEG-DSPE.

Example 13—Immunotherapy Using Subcutaneous and Sublingual Administrations

SCIT therapy: Allergy shots will be given in multiple dilutions (usually five bottles) which will be built up slowly over 8 to 10 months. They will be given once a week and after 8 months the patient will be switched to every other week and eventually every three to four weeks.

SLIT: diluted solutions from the allergy extracts will be created for allergy shots. The dilution will be made into 2 bottles with droppers. One less concentrated and one more concentrated.

Allergens (e.g., pollen peptides) encapsulated in the liposome preparation for SCIT and SLIT will be given once a week. Therapy will follow similar dosing regimens as conventional allergy shots. The liposome preparation will be similar to the procedures used in Example 1. In addition, comparison studies will be performed evaluated delivering single allergen versus multiple allergen therapy at one time with the delivery system.

| SCIT | Conventional Treatment | Delivery system given with encapsulated with a single pollen peptide | Delivery system encapsulated with several pollen/allergen peptides given at the same time |
|---|---|---|---|
| SLIT | Conventional Treatment | Delivery system given with encapsulated with a single pollen peptide | Delivery system encapsulated with several encapsulated pollen/allergen peptides given at the same time |

Bloodwork evaluating total IgE, skin testing to allergens, and IgG subclass will be monitored as markers to evaluate the response for therapy. SLIT therapy protocols will be comparable to conventional therapy such as allowing the patient to take the doses at home.

Example 14—Treating Tuberculosis

Four groups of experiments will be compared to evaluation the safety and efficacy of the pharmaceutical formulation in treating TB: untreated, placebo group, pH sensitive formulation (with Isoniazid, Gangamycin, or Streptomycin), and pH resistance formulation (with Isoniazid, Gangamycin, or Streptomycin).

| Untreated group | Placebo control to receive solution of similar volume once a week | pH sensitive formulation with Isoniazid given orally once a week | pH resistant formulation with Isoniazid given orally once a week |
|---|---|---|---|
| Untreated group | Placebo control to receive solution of similar volume once a week | pH sensitive formulation with Gangamycin given orally once a week | pH resistant formulation with Gangamycin given orally once a week |
| Untreated group | Placebo control to receive solution of similar volume once a week | pH sensitive formulation with Streptomycin given orally once a week | pH resistant formulation with Streptomycin given orally once a week |

The liposome preparation will be similar to the procedures used in Example 1. Dosage will administer per the standard dosing protocol for that particular drug. The drug will be encapsulated in the liposome carrier to be dosed once a week for a period of 6 weeks. Symptom scores will be recorded. Patients will be followed once a week to monitor them for urine and blood tests as well as examination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating inflammation associated with an allergy or a disease in a subject in need thereof, the method comprising administering, orally or sublingually, (1) a first active agent encapsulated in a first liposome carrier that comprises: i) poly (ethylene glycol) distearoylphosphatidylethanolamine (PEG-DSPE), ii) phosphatidylglycerol, phosphatidylcholine, or a combination thereof, and iii) a pH sensitive component which causes the liposome to release the first active agent in a pH range of about pH 1 to about pH 5; and (2) a second active agent encapsulated in a second liposome carrier that comprises: i) poly (ethylene glycol) distearoylphosphatidylethanolamine (PEG-DSPE), ii) phosphatidylglycerol, phosphatidylcholine, or a combination thereof, wherein the second liposome carrier releases the second active agent in a pH range of about pH 6 to about pH 8.

2. The method of claim 1, wherein the pH sensitive component comprises an acylated amino acid, a phospholipid, a fatty acid, a double chain amphiphile, cholesteryl hemisuccinate, or any combination thereof.

3. The method of claim 2, wherein the pH sensitive component comprises N-palmitoyl homocysteine (PHC).

4. The method of claim 1, wherein the first active agent, the second active agent, or both the first active agent and the second active agent comprise(s) a proton pump inhibitor, a corticosteroid, an antihistamine, a bronchodilator, a mast cell stabilizer, a leukotriene inhibitor, an allergen, or an anti-inflammatory agent.

5. The method of claim 4, wherein the anti-inflammatory agent comprise(s) theophylline, budesonide, flunisolide, triamcinolone, beclomethasone, fluticasone, mometasone, dexamethasone, hydrocortisone, methylprednisolone, prednisone, cortisone, or betamethasone.

6. The method of claim 1, wherein the first active agent and the second active agent are the same active agent.

7. The method of claim 1, wherein the first active agent and the second active agent are different active agents.

8. The method of claim 1, wherein the allergy is a food allergy, and wherein the first active agent comprises peanut, tree nut, egg, shellfish, soy, milk, gluten, or any combination thereof.

9. The method of claim 1, wherein the first active agent, the second active agent, or both the first active agent and the second active agent comprise an H1-antihistamine, an H2-antihistamine, an H3-antihistamine, or an H4-antihistamine.

10. The method of claim 9, wherein the H1-antihistamine comprises acrivastine, azelastine, bilastine, brompheniramine, buclizine, bromodiphenhydramine, carbinoxamine, chlorpromazine, cyclizine, chlorphenamine, chlorodiphenhydramine, clemastine, cyproheptadine, dexbrompheniramine, dexchlorpheniramine, dimenhydrinate, dimetindene, diphenhydramine, doxylamine, ebastine, embramine, fexofenadine, hydroxyzine, loratadine, meclozine, mirtazapine, olopatadine, orphenadrine, phenindamine, pheniramine, phenyltoloxamine, promethazine, quetiapine, rupatadine, tripelennamine, triprolidine, or any combination thereof.

11. The method of claim 1, wherein the first liposome carrier comprises from about 60% to about 99% phosphatidylcholine, phosphatidylglycerol, or any combination thereof.

12. The method of claim 1, wherein the second liposome carrier comprises from about 60% to about 99% phosphatidylcholine, phosphatidylglycerol, or any combination thereof.

13. The method of claim 1, wherein the first liposome carrier and the second liposome carrier comprise from about 1% to about 5% PEG-DSPE.

14. The method of claim 1, wherein the first liposome carrier and the second liposome carrier comprise from about 1% to about 33% of the first active agent.

15. The method of claim 1, wherein the first active agent, the second active agent, or both the first active agent and the second active agent comprise(s) an anti-tuberculosis agent.

16. The method of claim 1, wherein the first active agent, the second active agent, or both the first active agent and the second active agent comprise(s) an anti-IgE antibody or a fragment thereof.

17. The method of claim 1, wherein the first active agent, the second active agent, or both the first active agent and the second active agent comprise(s) a lyophilized powder.

18. The method of claim 1, wherein the disease is a chronic immune system disease, tuberculosis, or Eosinophilic esophagitis (EoE).

19. The method of claim 1, wherein the disease is tuberculosis.

20. The method of claim 15, wherein the anti-tuberculosis agent comprises isoniazid, ethambutol, pyrazinamide, rifamycin, rifampin, streptomycin, clarithromycin.

* * * * *